(12) United States Patent
Noguchi et al.

(10) Patent No.: US 10,703,880 B2
(45) Date of Patent: Jul. 7, 2020

(54) PLASTICIZER FOR VINYL CHLORIDE RESIN, VINYL CHLORIDE RESIN COMPOSITION, WIRE HARNESS, AND DASHBOARD

(71) Applicant: DIC Corporation, Tokyo (JP)

(72) Inventors: Takafumi Noguchi, Ichihara (JP); Akira Urabe, Ichihara (JP); Akio Toyoda, Ichihara (JP); Yoshiyuki Yaoita, Ichihara (JP); Tetsurou Umemoto, Ichihara (JP); Osamu Suzuki, Ichihara (JP)

(73) Assignee: DIC Corporation, Tokyo (JP)

( * ) Notice: Subject to any disclaimer, the term of this patent is extended or adjusted under 35 U.S.C. 154(b) by 75 days.

(21) Appl. No.: 15/751,960

(22) PCT Filed: Aug. 4, 2016

(86) PCT No.: PCT/JP2016/072936
§ 371 (c)(1),
(2) Date: Feb. 12, 2018

(87) PCT Pub. No.: WO2017/030000
PCT Pub. Date: Feb. 23, 2017

(65) Prior Publication Data
US 2018/0244894 A1 Aug. 30, 2018

(30) Foreign Application Priority Data
Aug. 19, 2015 (JP) .................................. 2015-161895

(51) Int. Cl.
| | |
|---|---|
| B32B 27/06 | (2006.01) |
| C08K 5/12 | (2006.01) |
| C07C 69/76 | (2006.01) |
| C08L 27/06 | (2006.01) |
| H01B 7/00 | (2006.01) |
| B62D 25/14 | (2006.01) |
| B60K 37/00 | (2006.01) |
| C07C 67/24 | (2006.01) |

(52) U.S. Cl.
CPC ............... C08K 5/12 (2013.01); B60K 37/00 (2013.01); B62D 25/14 (2013.01); C07C 67/24 (2013.01); C07C 69/76 (2013.01); C08L 27/06 (2013.01); H01B 7/00 (2013.01)

(58) Field of Classification Search
None
See application file for complete search history.

(56) References Cited

U.S. PATENT DOCUMENTS

| | | | | |
|---|---|---|---|---|
| 3,296,298 A | * | 1/1967 | Rowland ................. | C07C 69/76 524/298 |
| 4,317,760 A | * | 3/1982 | Tsuda ....................... | C08K 5/12 524/111 |
| 2016/0160020 A1 | * | 6/2016 | Matsuoka ............... | C08L 27/06 525/190 |

FOREIGN PATENT DOCUMENTS

| | | |
|---|---|---|
| EP | 0023363 A1 | 2/1981 |
| JP | 01-158060 A | 6/1989 |
| JP | 2014-189688 A | 10/2014 |

OTHER PUBLICATIONS

International Search Report dated Nov. 1, 2016, issued for PCT/JP2016/072936.
Guixin Shi et al., "Poly(epsilon-caprolactone)-based 'green' plasticizers for poly(vinyl choride)", Polymer Degradation and Stability, Barking, GB, vol. 96, No. 9, Jun. 17, 2011, pp. 1639-1647.(in the Apr. 12, 2019 Search Report issued for EP16836991.6).
Supplementary European Search Report dated Apr. 12, 2019, issued for the European patent application No. 16836991.6.

* cited by examiner

Primary Examiner — Robert T Butcher
(74) Attorney, Agent, or Firm — Locke Lord LLP

(57) ABSTRACT

The present invention provides a plasticizer for a vinyl chloride resin including an ester compound (A1) represented by General Formula (1):

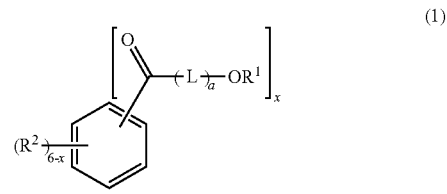

(in the formula, L's each represent an aliphatic oxycarboxylic acid residue having 3 to 18 carbon atoms or a cyclic ester residue having 3 to 18 carbon atoms, $R^1$'s each represent an alkyl group having 6 to 18 carbon atoms, $R^2$'s each represent a hydrogen atom or an alkyl group having 1 to 6 carbon atoms, a represents a repeating number of the L, provided that the total of the plural a's is from 1 to 10, and x is an integer of 2 to 4), in order to provide a plasticizer for a vinyl chloride which has excellent compatibility with vinyl chloride resins and with which a vinyl chloride resin composition capable of providing a molded article having excellent freeze resistance and heat resistance can be obtained.

14 Claims, No Drawings

PLASTICIZER FOR VINYL CHLORIDE RESIN, VINYL CHLORIDE RESIN COMPOSITION, WIRE HARNESS, AND DASHBOARD

TECHNICAL FIELD

The present invention relates to a plasticizer for a vinyl chloride resin, which has excellent compatibility with vinyl chloride resins and with which a vinyl chloride resin composition capable of providing a molded article having excellent freeze resistance and heat resistance is obtained. The present invention further relates to a vinyl chloride resin composition including the plasticizer for a vinyl chloride resin, a wire harness obtained by using the same, and a dashboard obtained by molding the vinyl chloride resin composition.

BACKGROUND ART

In many cases, vinyl chloride resins are used as a vinyl chloride resin composition in which a plasticizer is added in order to not only apply various performances such as flexibility, but also decrease working temperatures in various molding processes such as extruding or calendaring, thereby facilitating the molding processes.

It is desirable that the plasticizer used in such a vinyl chloride resin composition has performances of having excellent compatibility with vinyl chloride resins and providing a molded article of a vinyl chloride resin composition having excellent heat resistance and freeze resistance.

In the related art, as the plasticizer used in the vinyl chloride resin composition, a higher alkyl ester of a polybasic acid such as a phthalic acid diester, an adipic acid diester, or a trimellitic acid triester has been known, for example. In the related art, the phthalic acid diester is mainly used in many cases, by considering a price or a balance between performances of heat resistance and freeze resistance, but in recent years, the trimellitic acid triester has been used as the plasticizer, in the case where higher heat resistance is required. Specifically, the trimellitic acid triester such as tri-2-ethylhexyl trimellitate (hereinafter, abbreviated as "TOTM"), triisononyl trimellitate (hereinafter, abbreviated as "TINTM"), or triisodecyl trimellitate (hereinafter, abbreviated as "TIDTM") has excellent compatibility with vinyl chloride resins, and even in the case where a molded article obtained by using a vinyl chloride resin composition including the trimellitic acid triester is exposed in a heating environment, the mass thereof decreased is small (excellent heat aging resistance is obtained). Thus, the trimellitic acid triester is frequently used for heat resistant wires used at a temperature equal to or higher than 105° C. or dashboards for a car.

However, in recent years, the demand for freeze resistance or heat resistance becomes increasingly stronger, and it has been difficult to apply sufficient freeze resistance or heat resistance to a molded article by using the TOTM, the TINTM, and the TIDTM.

As the plasticizer for obtaining a vinyl chloride resin composition with which a molded article having excellent heat resistance and freeze resistance is obtained, for example, a plasticizer which is an esterified product of trimellitic acid and an aliphatic alcohol having 9 carbon atoms and in which a linear aliphatic alcohol and a branched aliphatic alcohol are used at a specific ratio as the aliphatic alcohol, has been known (for example, see PTL 1). However, the plasticizer has poor compatibility with vinyl chloride resins. Accordingly, the plasticizer bleeds out on a surface of a molded article obtained from a composition including the plasticizer and a vinyl chloride resin over time, and as a result, a problem regarding deteriorations in heat resistance and freeze resistance of a molded article over time is raised.

A polyester-based plasticizer has also been known as the plasticizer for obtaining a molded article of vinyl chloride resins. As the plasticizer for obtaining a molded body having excellent freeze resistance, specifically, a plasticizer with which flexibility of a molded body can be maintained even at a low temperature, a plasticizer obtained by causing a reaction between a glycol having a branched aliphatic structure, a cyclic ester having 3 to 18 carbon atoms or an aliphatic oxycarboxylic acid having 3 to 18 carbon atoms, a dibasic acid such as adipic acid, and a monoalcohol having 2 to 22 carbon atoms has been known (for example, see PTL 2). However, even in the case where the plasticizer disclosed in PTL 2 was used, it was difficult to apply sufficient freeze resistance to a molded article.

CITATION LIST

Patent Literature

[PTL 1] JP-A-2014-189688
[PTL 1] JP-A-1-158060

SUMMARY OF INVENTION

Technical Problem

An object of the present invention is to provide a plasticizer for a vinyl chloride resin, which has excellent compatibility with vinyl chloride resins and with which a vinyl chloride resin composition capable of providing a molded article having excellent freeze resistance and heat resistance is obtained. Another object of the present invention is to provide a wire harness and a dashboard by using the vinyl chloride resin composition.

Solution to Problem

As a result of intensive studies, the inventors have found that a polyester resin obtained by causing a reaction between benzenecarboxylic acid; an aliphatic oxycarboxylic acid having 3 to 18 carbon atoms or a cyclic ester having 3 to 18 carbon atoms; and a saturated aliphatic monoalcohol having 6 to 18 carbon atoms can be used as a plasticizer of vinyl chloride resins, a molded article obtained by using a composition including the polyester resin and a vinyl chloride resin can maintain heat resistance or freeze resistance, specifically, plasticity, even in the case of being exposed in a high temperature environment or a low temperature environment, the polyester resin has excellent compatibility with vinyl chloride resins and can maintain plasticity of vinyl chloride resins, even in the case of being exposed in a high temperature environment or a low temperature environment for a long period of time, and the composition can be preferably used for a molding material in the case of obtaining a dashboard or for coating of a wire such as a wire harness, thereby completing the present invention.

That is, according to the present invention, there is provided a plasticizer for a vinyl chloride resin, including an ester compound (A1) represented by General Formula (1).

[Chem. 1]

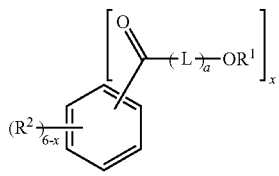
(1)

(In the formula, x is an integer of 2 to 4, plural L's may be the same or different, plural $R^1$'s may be the same or different, plural $R^2$'s may be the same or different, L's each represent an aliphatic oxycarboxylic acid residue having 3 to 18 carbon atoms or a cyclic ester residue having 3 to 18 carbon atoms, $R^1$'s each represent an alkyl group having 6 to 18 carbon atoms, $R^2$'s each represent a hydrogen atom or an alkyl group having 1 to 6 carbon atoms, and plural a's each represents a repeating number of L, provided that the total of the plural a's is from 1 to 10.)

In addition, according to the present invention, there is provided a vinyl chloride resin composition including the plasticizer for a vinyl chloride resin (X) and a vinyl chloride resin (Y).

Further, according to the present invention, there is provided a wire harness obtained by coating a wire with the vinyl chloride resin composition.

Furthermore, according to the present invention, there is provided a dashboard obtained by molding the vinyl chloride resin composition.

Advantageous Effects of Invention

The plasticizer for a vinyl chloride resin of the present invention can provide a vinyl chloride resin composition having excellent compatibility with vinyl chloride resins and capable of maintaining plasticity, even in the case of being exposed in a high temperature environment or a low temperature environment. In addition, the vinyl chloride resin composition of the present invention can be used for various applications such as wiring coating materials, automobile parts, imitation leather, boots, gaskets, and hoses. The vinyl chloride resin composition of the present invention can be particularly suitably used as wiring coating materials, particularly, coating materials used in preparing of a wire harness or molding materials used in preparing of a dashboard.

DESCRIPTION OF EMBODIMENTS

A plasticizer for a vinyl chloride resin of the present invention includes an ester compound (A1) represented by General Formula (1).

[Chem. 2]

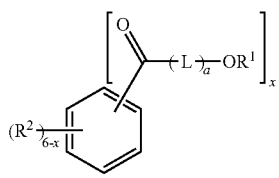
(1)

(In the formula, x is an integer of 2 to 4, plural L's may be the same or different, plural $R^1$'s may be the same or different, plural $R^2$'s may be the same or different, L's each represent an aliphatic oxycarboxylic acid residue having 3 to 18 carbon atoms or a cyclic ester residue having 3 to 18 carbon atoms, $R^1$'s each represent an alkyl group having 6 to 18 carbon atoms, $R^2$'s each represent a hydrogen atom or an alkyl group having 1 to 6 carbon atoms, and plural a's each represents a repeating number of L, provided that the total of the plural a's is from 1 to 10.)

As for L's, examples of the aliphatic oxycarboxylic acid residue having 3 to 18 carbon atoms include aliphatic monooxymonocarboxylic acid residues such as a lactic acid residue, a ω-oxycaproic acid residue, a ω-oxalauric acid residue, a ω-oxypalmitic acid residue, a ricinoleic acid residue, a 9-hydroxystearic acid residue, a 12-hydroxystearic acid residue, a hydrogenated castor oil fatty acid residue, and a hydrogenated castor oil residue.

As for L's, examples of the cyclic ester residue having 3 to 18 carbon atoms include a β-propiolactone residue, a r-butyrolactone residue, a δ-valerolactone residue, a γ-valerolactone residue, a ε-caprolactone residue, a methyl-ε-caprolactone residue, a dimethyl-ε-caprolactone residue, and a trimethyl-ε-caprolactone residue.

In the present invention, the number of carbon atoms in the wordings "aliphatic oxycarboxylic acid having 3 to 18 carbon atoms" or the "cyclic ester having 3 to 18 carbon atoms" includes the number of carbon atoms of a carbonyl group.

In the present invention, in the case where the aliphatic oxycarboxylic acid and the cyclic ester are represented by General Formula (α-1) and General Formula (α-2), respectively, the "aliphatic oxycarboxylic acid residue" and the "cyclic ester residue" are a structure represented by General Formula (α-3).

[Chem. 3]

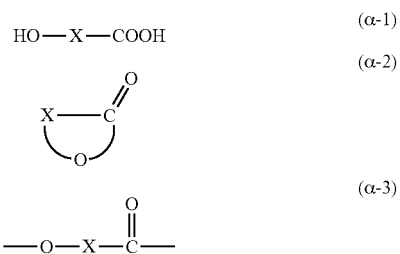

(In the formulae, X is an aliphatic structure having 2 to 17 carbon atoms.)

As for L's, an aliphatic oxycarboxylic acid residue having 4 to 13 carbon atoms or a cyclic ester residue having 4 to 13 carbon atoms is preferable, an aliphatic oxycarboxylic acid residue having 5 to 7 carbon atoms or a cyclic ester residue having 5 to 7 carbon atoms is respectively more preferable, and ε-caprolactone is even more preferable, from viewpoints of exhibiting excellent compatibility with vinyl chloride resins and obtaining a vinyl chloride resin composition capable of providing a molded article having excellent heat resistance and freeze resistance. The plural L's in General Formula (1) may be the same as each other or different from each other. With respect to L in the parentheses adjacent to a in General Formula (1), plural L's may be the same as each other or may include two or more kinds thereof mixedly.

$R^1$ in General Formula (1) is an alkyl group having 6 to 18 carbon atoms. Examples of the alkyl group include a hexyl group, an octyl group, a nonyl group, a decyl group, an undecyl group, a dodecyl group, a tridecyl group, a tetradecyl group, a pentadecyl group, a hexadecyl group, an octadecyl group, and an isotridecyl group. Among these, an alkyl group having 6 to 14 carbon atoms is preferable, from viewpoints of exhibiting excellent compatibility with vinyl chloride resins and obtaining a vinyl chloride resin composition capable of providing a molded article having excellent heat resistance and freeze resistance.

More specifically, in the case where the ester compound (A1) is an ester compound represented by General Formula (2) which will be described later, $R^{12}$ [corresponding to $R^1$ in General Formula (1)] in the formula represented by General Formula (2) is preferably an alkyl group having 7 to 14 carbon atoms and more preferably an alkyl group having 10 to 14 carbon atoms, from viewpoints of exhibiting excellent compatibility with vinyl chloride resins and obtaining a vinyl chloride resin composition capable of providing a molded article having excellent heat resistance and freeze resistance.

In the case where the ester compound (A1) is an ester compound represented by General Formula (3) which will be described later, $R^{13}$ [corresponding to $R^1$ in General Formula (1)] in the formula represented by General Formula (3) is preferably an alkyl group having 7 to 14 carbon atoms and more preferably an alkyl group having 7 to 12 carbon atoms, from viewpoints of exhibiting excellent compatibility with vinyl chloride resins and obtaining a vinyl chloride resin composition capable of providing a molded article having excellent heat resistance and freeze resistance.

In the case where the ester compound (A1) is an ester compound represented by General Formula (4) which will be described later, $R^{14}$ [corresponding to $R^1$ in General Formula (1)] in the formula represented by General Formula (4) is preferably an alkyl group having 6 to 13 carbon atoms and more preferably an alkyl group having 7 to 12 carbon atoms, from viewpoints of exhibiting excellent compatibility with vinyl chloride resins and obtaining a vinyl chloride resin composition capable of providing a molded article having excellent heat resistance and freeze resistance.

$R^2$ in the formula represented by General Formula (1) is a hydrogen atom or an alkyl group having 1 to 6 carbon atoms. Examples of the alkyl group include a methyl group, an ethyl group, a propyl group, a butyl group, an isopropyl group, and a t-butyl group. Among these, a hydrogen atom is preferable, from viewpoints of exhibiting excellent compatibility with vinyl chloride resins, and obtaining an inexpensive vinyl chloride resin composition capable of providing a molded article having excellent heat resistance and freeze resistance. The number of $R^2$'s in the formula represented by General Formula (1) is "6-x (x is an integer of 2 to 4)". For example, in a formula represented by General Formula (2) which will be described later, the number of $R^2$'s is 4 and therefore, "—$(R^2)_4$" is expressed in the formula represented by General Formula (2). In addition, in a formula represented by General Formula (3) which will be described later, the number of $R^2$'s is 3 and therefore, "—$(R^2)_3$" is expressed in the formula represented by General Formula (3). The plural $R^2$'s may be the same as each other or different from each other.

a in the formula represented by General Formula (1) is the repeating number of the L and the total of the plural a's is from 1 to 10. In the case where the ester compound (A1) in the plasticizer for a vinyl chloride resin of the present invention is obtained by a preparation method which will be described later, the ester compound (A1) generally becomes a mixture of ester compounds having different repeating numbers of L (the compounds being different in the total of the plural a's). The total of the plural a's is preferably 1 to 8 and more preferably 1 to 4, from viewpoints of exhibiting excellent compatibility with vinyl chloride resins and obtaining a vinyl chloride resin composition capable of providing a molded article having excellent heat resistance and freeze resistance.

More specifically, in the case where the ester compound (A1) is an ester compound represented by General Formula (2) which will be described later, the total of $a_{21}$ and $a_{22}$ in the formula represented by General Formula (2) is preferably 1 to 8 and more preferably 1 to 4.

In the case where the ester compound (A1) is an ester compound represented by General Formula (3) which will be described later, the total of $a_{31}$, $a_{32}$, and $a_{33}$ in the formula represented by General Formula (3) is preferably 1 to 6 and more preferably 1 to 3.

In the case where the ester compound (A1) is an ester compound represented by General Formula (4) which will be described later, the total of $a_{41}$, $a_{42}$, $a_{43}$, and $a_{44}$ in the formula represented by General Formula (4) is preferably 1 to 6 and more preferably 1 to 3.

The ester compound (A1), which is normally a mixture as described above, preferably includes an ester compound in which the total of a's is 1 to 3 in an amount of 10% to 100%, more preferably 20% to 70%, and even more preferably 20% to 50% with respect to the ester compound (A1), from viewpoints of exhibiting excellent compatibility with vinyl chloride resins and obtaining a vinyl chloride resin composition capable of providing a molded article having excellent heat resistance and freeze resistance.

More specifically, in the case where the plasticizer for a vinyl chloride resin of the present invention includes an ester compound represented by General Formula (2) which will be described later, the ester compound preferably includes an ester compound in which the total of $a_{21}$ and $a_{22}$ is 1 to 3 in an amount of 10% to 100%, more preferably 20% to 70%, and even more preferably 20% to 50%, from viewpoints of exhibiting excellent compatibility with vinyl chloride resins and obtaining a vinyl chloride resin composition capable of providing a molded article having excellent heat resistance and freeze resistance.

In the case where the plasticizer for a vinyl chloride resin of the present invention includes an ester compound represented by General Formula (3) which will be described later, the ester compound preferably includes an ester compound in which the total of $a_{31}$, $a_{32}$, and $a_{33}$ is 1 or 2 in an amount of 10% to 100%, more preferably 20% to 90%, and even more preferably 30% to 80%, from viewpoints of exhibiting excellent compatibility with vinyl chloride resins and obtaining a vinyl chloride resin composition capable of providing a molded article having excellent heat resistance and freeze resistance.

In the case where the plasticizer for a vinyl chloride resin of the present invention includes an ester compound represented by General Formula (4) which will be described later, the ester compound preferably includes an ester compound in which the total of $a_{41}$, $a_{42}$, $a_{43}$, and $a_{44}$ is 1 or 2 in an amount of 10% to 100%, more preferably 20% to 90%, and even more preferably 30% to 80%, from viewpoints of exhibiting excellent compatibility with vinyl chloride resins and obtaining a vinyl chloride resin composition capable of providing a molded article having excellent heat resistance and freeze resistance.

In addition, in the case where the plasticizer for a vinyl chloride resin of the present invention is a mixture of ester compounds obtained by mixing two or more kinds in which X's which are 2, 3, or 4, as the ester compound (A1) in General Formula (1), taking the total amount of the ester compounds having the same X as 100%, a percentage of the ester compounds having the same total value of a's is respectively calculated. For example, in the case where the plasticizer for a vinyl chloride resin of the present invention includes ester compounds in which X is 2 and ester compounds in which X is 3 in General Formula (1), the content of the ester compounds in which X is 2 and the content of the ester compounds in which X is 3 are obtained, respectively. Then, a percentage of ester compounds having the same total value of a's with respect to the ester compounds in which X is 2 is obtained taking the content of the ester compound in which X is 2 as 100%. The thus-obtained percentages preferably apply to the preferred ranges described above.

Here, the content (presence ratio) of each of the ester compounds which are different in the total of a's, in the ester compound (A1) (mixture) can be obtained from a percentage of a peak area with respect to each molecular weight obtained by gel permeation chromatography (GPC) measurement shown below.

[GPC Measurement Conditions]

Measurement device: High-speed GPC device "HLC-8320 GPC" manufactured by Tosoh Corporation Column: "TSK GURDCOLUMN Super HZ-L" manufactured by Tosoh Corporation+"TSK gel Super HZM-M" manufactured by Tosoh Corporation+"TSK gel Super HZM-M" manufactured by Tosoh Corporation+"TSK gel SuperHZ-2000" manufactured by Tosoh Corporation+"TSK gel SuperHZ-2000" manufactured by Tosoh Corporation Detector: RI (differential refractometer)

Data processing: "EcoSEC Data Analysis version 1.07" manufactured by Tosoh Corporation Column temperature: 40° C.

Eluent: Tetrahydrofuran

Flow rate: 0.35 mL/min

Measurement sample: 15 mg of a sample was dissolved in 10 ml of tetrahydrofuran, the obtained solvent was filtered with a micro filter, and the resultant material was set as a measurement sample.

Sample injection amount: 20 μl

Reference sample: the following monodisperse polystyrenes having well-known molecular weight were used based on a measurement manual of the "HLC-8320 GPC".

(monodisperse polystyrenes)

"A-300" manufactured by Tosoh Corporation
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
"F-288" manufactured by Tosoh Corporation The plasticizer for a vinyl chloride resin of the present invention includes the ester compound (A1) as described above. The content of the ester compound (A1) in the plasticizer for a vinyl chloride resin of the present invention is preferably 10% to 100% by mass, more preferably 30% to 100% by mass, even more preferably 50% to 100% by mass, and still more preferably 70% to 100% by mass, from viewpoints of facilitating the production and exhibiting the effects of the invention (exhibiting excellent compatibility with vinyl chloride resins and obtaining a vinyl chloride resin composition capable of providing a molded article having excellent heat resistance and freeze resistance).

As the ester compound (A1) represented by General Formula (1), an ester compound (A2) in which X in General Formula (1) is 2, an ester compound (A3) in which X in General Formula (1) is 3, and an ester compound (A4) in which X in General Formula (1) is 4 are used.

[Chem. 4]

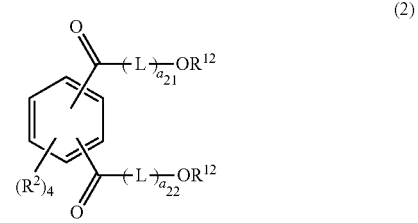

(2)

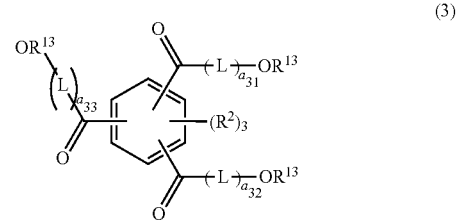

(3)

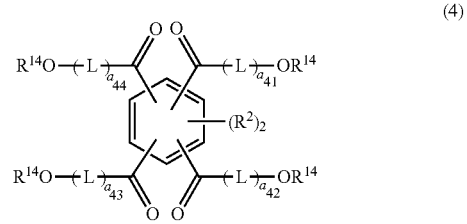

(4)

In the ester compound (A2) represented by General Formula (2), L's and $R^2$ are the same as those described above. The total of $a_{21}$ and $a_{22}$ is from 1 to 10. $R^{12}$'s are an alkyl group having 6 to 18 carbon atoms. In the ester compound (A3) represented by General Formula (3), L's and $R^2$ are the same as those described above. The total of $a_{31}$, $a_{32}$, and $a_{33}$ is from 1 to 10. $R^{13}$'s each are an alkyl group having 6 to 18 carbon atoms. In the ester compound (A4) represented by General Formula (4), L's and $R^2$ are the same as those described above. The total of $a_{41}$, $a_{42}$, $a_{43}$, and $a_{44}$ is from 1 to 10. $R^{14}$'s each are an alkyl group having 6 to 18 carbon atoms.

As the ester compound (A2) represented by General Formula (2), ester compounds represented by General Formula (2-1) to General Formula (2-3) are usable.

[Chem. 5]

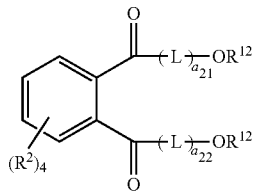
(2-1)

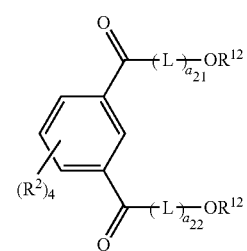
(2-2)

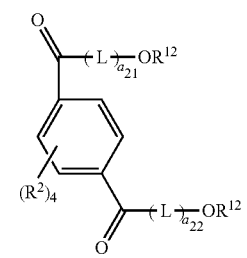
(2-3)

As the ester compound (A3) represented by General Formula (3), ester compounds represented by General Formula (3-1) to General Formula (3-3) are usable. Among these, the ester compound represented by General Formula (3-1) is preferable.

[Chem. 6]

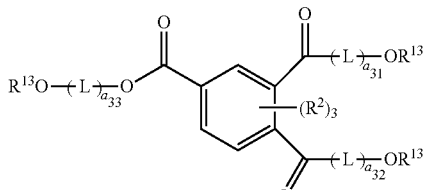
(3-1)

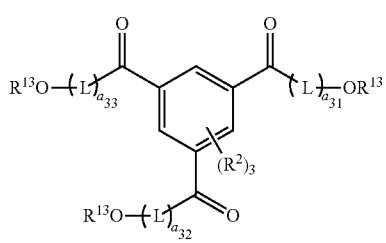
(3-2)

(3-3)

As the ester compound (A4) represented by General Formula (4), ester compounds represented by General Formula (4-1) to General Formula (4-3) are usable.

[Chem. 7]

(4-1)

(4-2)

(4-3)

Among the ester compounds (A1) represented by General Formula (1), the ester compound (A3) in which X in General Formula (1) is 3 or the ester compound (A4) in which X is 4 is preferable, from the viewpoint of obtaining a vinyl chloride resin composition with which a molded article having excellent oil resistance is obtained.

The raw materials for the ester compound (A1), for example, include one or more kinds of compounds (a1) selected from the group consisting of divalent to tetravalent benzenecarboxylic acid, alkyl esters thereof, and anhydrides thereof; one or more kinds of compounds (a2) selected from the group consisting of an aliphatic oxycarboxylic acid having 3 to 18 carbon atoms, an alkyl ester of an aliphatic oxycarboxylic acid having 3 to 18 carbon atoms, and a cyclic ester having 3 to 18 carbon atoms; and a saturated aliphatic monoalcohol (a3) having 6 to 18 carbon atoms. Specifically, the ester compound (A1) can be prepared, for example, by causing a reaction between one or more kinds of compounds (a1) selected from the group consisting of divalent to tetravalent benzenecarboxylic acid, alkyl esters thereof, and anhydrides thereof, one or more kinds of compounds (a2) selected from the group consisting of an aliphatic oxycarboxylic acid having 3 to 18 carbon atoms, an alkyl ester of an aliphatic oxycarboxylic acid having 3 to 18 carbon atoms, and a cyclic ester having 3 to 18 carbon atoms, and a saturated aliphatic monoalcohol (a3) having 6 to 18 carbon atoms.

Examples of the divalent benzenecarboxylic acid (benzenedicarboxylic acid), an alkyl ester of a benzenedicarboxylic acid, and an anhydride of a benzenedicarboxylic acid include phthalic acid, 4-methylphthalic acid, isophthalic acid, terephthalic acid, alkyl esters thereof, and acid anhydrides of phthalic acid and 4-methylphthalic acid. Among these, one or more kinds of compounds selected from the group consisting of phthalic acid, isophthalic acid, terephthalic acid, alkyl esters thereof, and phthalic acid anhydride are preferable, from viewpoints of exhibiting excellent compatibility with vinyl chloride resins and obtaining a vinyl chloride resin composition capable of providing a molded article having excellent heat resistance and freeze resistance. The benzenedicarboxylic acid may be used alone or in combination of two or more kinds thereof.

Examples of the trivalent benzenecarboxylic acid (benzenetricarboxylic acid), an alkyl ester of a benzenetricarboxylic acid, and an anhydride of a benzenetricarboxylic acid include 1,3,5-benzenetricarboxylic acid, 1,2,4-benzenetricarboxylic acid, 1,2,3-benzenetricarboxylic acid, 3-methyl-1,2,4-benzenetricarboxylic acid, 3,5-dimethyl-1,2,4-benzenetricarboxylic acid, 3,5,6-trimethyl-1,2,4-benzenetricarboxylic acid, an alkyl ester thereof, and an acid anhydride thereof. Among these, one or more kinds of compounds selected from the group consisting of 1,2,4-benzenetricarboxylic acid, an alkyl ester thereof, and an acid anhydride thereof are preferable, from viewpoints of exhibiting excellent compatibility with vinyl chloride resins and obtaining a vinyl chloride resin composition capable of providing a molded article having excellent heat resistance and freeze resistance. The benzenetricarboxylic acid may be used alone or in combination of two or more kinds thereof.

Examples of the tetravalent benzenecarboxylic acid (benzenetetracarboxylic acid), an alkyl ester of a benzenetetracarboxylic acid, and an anhydride of a benzenetetracarboxylic acid include 1,2,4,5-benzenetetracarboxylic acid, 1,2,3,5-benzenetetracarboxylic acid, 1,2,3,4-benzenetetracarboxylic acid, 3-methyl-1,2,4,5-benzenetetracarboxylic acid, and 3,6-dimethyl-1,2,4,5-benzenetetracarboxylic acid. Among these, one or more kinds of compounds selected from the group consisting of 1,2,4,5-benzenetetracarboxylic acid, an alkyl ester thereof, and an acid anhydride thereof are preferable, from viewpoints of exhibiting excellent compatibility with vinyl chloride resins and obtaining a vinyl chloride resin composition capable of providing a molded article having excellent heat resistance and freeze resistance. The benzenetetracarboxylic acid may be used alone or in combination of two or more kinds thereof.

Examples of the aliphatic oxycarboxylic acid having 3 to 18 carbon atoms and an alkyl ester of the aliphatic oxycarboxylic acid having 3 to 18 carbon atoms include an aliphatic oxycarboxylic acid such as lactic acid, ω-oxycaproic acid, ω-oxalauric acid, ω-oxypalmitic acid, ricinoleic acid, 9-hydroxystearic acid, 12-hydroxystearic acid, and a hydrogenated castor oil fatty acid, or an alkyl ester thereof.

Examples of the cyclic ester having 3 to 18 carbon atoms include β-propiolactone, r-butyrolactone, δ-valerolactone, γ-valerolactone, ε-caprolactone, methyl-ε-caprolactone, dimethyl-ε-caprolactone, and trimethyl-ε-caprolactone.

As for (a2), one or more kinds of compounds selected from the group consisting of an aliphatic oxycarboxylic acid having to 13 carbon atoms, an alkyl ester of the aliphatic oxycarboxylic acid having 4 to 13 carbon atoms, and a cyclic ester having 5 to 7 carbon atoms are preferable, an aliphatic oxycarboxylic acid having 5 to 7 carbon atoms, an alkyl ester of the aliphatic oxycarboxylic acid having 5 to 7 carbon atoms, and a cyclic ester having 5 to 7 carbon atoms are more preferable, and ε-caprolactone is even more preferable, from viewpoints of exhibiting excellent compatibility with vinyl chloride resins and obtaining a vinyl chloride resin composition capable of providing a molded article having excellent heat resistance and freeze resistance. One or more kinds of compounds (a2) selected from the group consisting of the aliphatic oxycarboxylic acid having 3 to 18 carbon atoms, the alkyl ester of the aliphatic oxycarboxylic acid having 3 to 18 carbon atoms, and the cyclic ester having 3 to 18 carbon atoms may be used alone or in combination of two or more kinds thereof.

Examples of the saturated aliphatic monoalcohol (a3) having 6 to 18 carbon atoms include hexanol, isohexanol, heptanol, n-octanol, isooctanol, 2-ethylhexanol, nonanol, isononanol, 2-methyloctanol, decanol, isodecanol, undecanol, dodecanol, tridecanol, isotridecanol, tetradecanol, pentadecanol, hexadecanol, and octadecanol.

As for the saturated aliphatic monoalcohol (a3), a saturated aliphatic monoalcohol having 7 to 14 carbon atoms is preferable and a saturated aliphatic monoalcohol having 8 to 14 carbon atoms is more preferable, from viewpoints of exhibiting excellent compatibility with vinyl chloride resins and obtaining a vinyl chloride resin composition capable of providing a molded article having excellent heat resistance and freeze resistance.

More specifically, in the case where the ester compound (A1) is the ester compound (A2) represented by General Formula (2), the saturated aliphatic monoalcohol (a3) is preferably a saturated aliphatic monoalcohol having 7 to 14 carbon atoms, more preferably a saturated aliphatic monoalcohol having 10 to 14 carbon atoms, and even more preferably one or more kinds of alcohols selected from the group consisting of dodecanol, tetradecanol, and isotridecanol.

In the case where the ester compound (A1) is the ester compound (A3) represented by General Formula (3), the saturated aliphatic monoalcohol (a3) is preferably a saturated aliphatic monoalcohol having 7 to 14 carbon atoms, more preferably a saturated aliphatic monoalcohol having 7 to 12 carbon atoms, and even more preferably one or more kinds of alcohols selected from the group consisting of n-octanol, nonanol, isononanol, decanol, undecanol, and dodecanol. In addition, in the case where the ester compound (A1) is the ester compound (A4) represented by General Formula (4), the saturated aliphatic monoalcohol (a3) is preferably a saturated aliphatic monoalcohol having 6 to 13 carbon atoms, more preferably a saturated aliphatic monoalcohol having 7 to 12 carbon atoms, and even more preferably one or more kinds of alcohols selected from the group consisting of n-octanol, nonanol, isononanol, decanol, undecanol, and dodecanol.

In the case of causing a reaction between one or more kinds of compounds (a1) selected from the group consisting of divalent to tetravalent benzenecarboxylic acid, alkyl esters thereof, and anhydrides thereof, one or more kinds of compounds (a2) selected from the group consisting of an aliphatic oxycarboxylic acid having 3 to 18 carbon atoms, an alkyl ester of an aliphatic oxycarboxylic acid having 3 to 18 carbon atoms, and a cyclic ester having 3 to 18 carbon atoms, and a saturated aliphatic monoalcohol having 6 to 18 carbon atoms (a3), the (a1), the (a2), and the (a3) may be collectively put into a reaction system to cause a reaction, or the (a1) and the (a2) may be put into a reaction system to cause a reaction, thereby obtaining a reactant, and then, the (a3) may be added to the reaction system to cause a reaction between the reactant and the (a3).

Specifically, the ester compound (A1) can be prepared by causing an esterification reaction of the (a1), the (a2), and the (a3), if necessary, under the presence of an esterification catalyst, for example, in a temperature range of 100° C. to 250° C. for 2 to 25 hours. The conditions such as the temperature and the time of the esterification reaction are not particularly limited and may be suitably set.

Examples of the esterification catalyst include a titanium-based catalyst such as tetraisopropyl titanate or tetrabutyl titanate; a tin-based catalyst such as dibutyl tin oxide; and an organic sulfonic acid-based catalyst such as p-toluenesulfonic acid.

The amount of the esterification catalyst used may be suitably set, and is normally preferably in a range of 0.001 to 0.1 parts by mass with respect to 100 parts by mass of the total amount of raw materials.

The amount of the (a2) used with respect to the amount of (a1) is preferably 0.1 to 6 mol and more preferably 0.2 to 4 mol with respect to 1 mol of a carboxyl group included in the (a1), from viewpoints of exhibiting excellent compatibility with vinyl chloride resins and obtaining a vinyl chloride resin composition capable of providing a molded article having excellent heat resistance and freeze resistance. More specifically, in the case where the (a1) is one or more kinds of compounds selected from the group consisting of a benzenedicarboxylic acid, an alkyl ester thereof, and an anhydride thereof, the amount of the (a2) used with respect to the amount of (a1) is preferably 1 to 4 mol and more preferably 2 to 3 mol with respect to 1 mol of the (a1). In the case where the (a1) is one or more kinds of compounds selected from the group consisting of a benzenetricarboxylic acid, an alkyl ester thereof, and an anhydride thereof, the amount of the (a2) used with respect to the amount of (a1) is preferably 0.3 to 4.5 mol and more preferably 0.6 to 3 mol with respect to 1 mol of the (a1). In the case where the (a1) is one or more kinds of compounds selected from the group consisting of a benzenetetracarboxylic acid, an alkyl ester thereof, and an anhydride thereof, the amount of the (a2) used with respect to the amount of (a1) is preferably 0.4 to 6 mol and more preferably 0.8 to 4 mol with respect to 1 mol of the (a1).

In addition, the amount of the (a3) used with respect to the amount of (a1) is preferably 2 to 6 mol and more preferably 2 to 4.8 mol with respect to 1 mol of a carboxyl group included in the (a1), from viewpoints of exhibiting excellent compatibility with vinyl chloride resins and obtaining a vinyl chloride resin composition capable of providing a molded article having excellent heat resistance and freeze resistance. More specifically, in the case where the (a1) is one or more kinds of compounds selected from the group consisting of a benzenedicarboxylic acid, an alkyl ester thereof, and an anhydride thereof, the amount of the (a3) used with respect to the amount of (a1) is preferably 2 to 3 mol and more preferably 2 to 2.4 mol with respect to 1 mol of the (a1). In the case where the (a1) is one or more kinds of compounds selected from the group consisting of a benzenetricarboxylic acid, an alkyl ester thereof, and an anhydride thereof, the amount of the (a3) used with respect to the amount of (a1) is preferably 3 to 4.5 mol and more preferably 3 to 3.6 mol with respect to 1 mol of the (a1). In the case where the (a1) is one or more kinds of compounds selected from the group consisting of a benzenetetracarboxylic acid, an alkyl ester thereof, and an anhydride thereof, the amount of the (a3) used with respect to the amount of (a1) is preferably 4 to 6 mol and more preferably 4 to 4.8 mol with respect to 1 mol of the (a1).

The plasticizer for a vinyl chloride resin of the present invention may include other plasticizers for vinyl chloride resins, together with the ester compound (A1). As such a plasticizer, an ester compound (B) of one or more kinds of compounds selected from the group consisting of an aromatic carboxylic acid, an alkyl ester thereof, and an anhydride thereof, and a saturated aliphatic monoalcohol having 4 to 12 carbon atoms can be preferably exemplified, for example.

As one or more kinds of compounds selected from the group consisting of the aromatic carboxylic acid, an alkyl ester thereof, and an anhydride thereof, a benzenemonocarboxylic acid such as benzoic acid, besides the benzenedicarboxylic acid, the benzenetricarboxylic acid, the benzenetetracarboxylic acid, an alkyl ester thereof, and an anhydride thereof, may be used. Examples of the saturated aliphatic monoalcohol include butanol, isobutanol, pentanol, hexanol, isohexanol, heptanol, n-octanol, isooctanol, 2-ethylhexanol, nonanol, isononanol, 2-methyloctanol, decanol, isodecanol, undecanol, and dodecanol.

Examples of the ester compound (B) include benzoic acid esters such as diethylene glycol dibenzoate; phthalic acid esters such as dibutyl phthalate (DBP), di-2-ethylhexyl phthalate (DOP), diisononyl phthalate (DINP), diisodecyl phthalate (DIDP), diundecyl phthalate (DUP), and ditridecyl phthalate (DTDP); terephthalic acid esters such as bis(2-ethylhexyl) terephthalate (DOTP); isophthalic acid esters such as bis(2-ethylhexyl) isophthalate (DOIP); trimellitic acid esters such as tri-2-ethylhexyl trimellitate (TOTM), triisononyl trimellitate (TINTM), and triisodecyl trimellitate (TIDTM); and pyromellitic acid esters such as tetra-2-ethylhexy pyromellitate (TOPM).

As for ester compound (B), it is preferable to use an ester compound of one or more kinds of compounds selected from the group consisting of trimellitic acid, pyromellitic acid, an alkyl ester thereof and an anhydride thereof, and a saturated aliphatic monoalcohol having 6 to 9 carbon atoms, from viewpoints of obtaining a plasticizer for a vinyl chloride resin, which has excellent compatibility with vinyl chloride resins and hardly moves to other article which is in contact therewith. Among these, an ester compound of trimellitic acid and 2-ethylhexanol [tri-2-ethylhexyl trimellitate (TOTM)] and an ester compound of pyromellitic acid and 2-ethylhexanol [tetra-2-ethylhexyl pyromellitate (TOPM)] are more preferable.

In the case where the ester compound (B) is added to the plasticizer for a vinyl chloride resin of the present invention, the amount thereof used is preferably 10 to 300 parts by mass and more preferably 20 to 200 parts by mass with respect to 100 parts by mass of the ester compound (A1).

A plasticizer other than the ester compound (B) may also be further added to the plasticizer for a vinyl chloride resin of the present invention within a range not deteriorating the effects of the invention. Examples of the plasticizer other than the ester compound (B) include aliphatic dibasic acid esters such as di-2-ethylhexyl adipate (DOA), diisononyl adipate (DINA), diisodecyl adipate (DIDA), di-2-ethylhexyl sebacate (DOS), and diisononyl sebacate (DINS);

phosphoric acid esters such as tri-2-ethylhexyl phosphate (TOP), and tricresyl phosphate (TCP); alkyl esters of polyhydric alcohols such as pentaerythritol; polyesters having molecular weight of 800 to 4,000 synthesized by polyesterification of a dibasic acid such as adipic acid and glycol; epoxidized esters such as epoxidized soybean oil and epoxidized linseed oil; alicyclic dibasic acids such as a hexahydrophthalic acid diisononyl ester; fatty acid glycol esters such as 1,4-butanediol dicaprylate; tributyl acetylcitrates (ATBC); chlorinated paraffins obtained by chlorination of a paraffin wax or n-paraffin; chlorinated fatty acid esters such as chlorinated stearic acid esters; and higher fatty acid esters such as butyl oleate.

The vinyl chloride resin composition of the invention includes the plasticizer for a vinyl chloride resin (X) and the vinyl chloride resin (Y).

Examples of the vinyl chloride resin (Y) include a homopolymer of vinyl chloride, a homopolymer of vinylidene chloride, a copolymer including vinyl chloride as an essential component, and a copolymer including vinylidene chloride as an essential component. The vinyl chloride resin (Y) may be obtained by various well-known preparation methods. Examples of the preparation methods include a method of suspension polymerization under the presence of an oil-soluble polymerization catalyst, and a method of emulsion polymerization under the presence of a water-soluble polymerization catalyst in aqueous media. A degree of polymerization of the vinyl chloride resin (Y) is normally 300 to 5,000 and preferably 400 to 3,500. The degree of polymerization thereof is preferably 700 to 3,000, from viewpoints of obtaining a vinyl chloride resin composition having excellent workability with which a molded article having high heat resistance is obtained.

As for vinyl chloride resin (Y), examples of the copolymer include a copolymer of polyfunctional monomers such as α-olefins having 2 to 30 carbon atoms such as ethylene, propylene, 1-butene, 1-pentene, 1-hexene, 1-heptene, 1-octene, 1-nonene, 1-decene, 1-undecene, 1-dodecene, 1-tridecene, and 1-tetradecene, acrylic acid and esters thereof, methacrylic acid and esters thereof, maleic acid and esters thereof, a vinyl compound such as vinyl acetate, vinyl propionate, or an alkyl vinyl ether, and diallyl phthalate, and a mixture thereof and a vinyl chloride monomer; an ethylene-acrylic acid ester copolymer such as an ethylene-ethyl acrylate copolymer; an ethylene-methacrylic acid ester copolymer; an ethylene-vinyl acetate copolymer (EVA); and a graft copolymer obtained by grafting a vinyl chloride monomer to a chlorinated polyethylene, butyl rubber, a crosslinked acrylic rubber, polyurethane, a butadiene-styrene-methyl methacrylate copolymer (MBS), a butadiene-acrylonitrile-(α-methyl) styrene copolymer (ABS), a styrene-butadiene copolymer, polyethylene, polymethyl methacrylate, and a mixture thereof.

A content of the plasticizer for a vinyl chloride resin (X) in the vinyl chloride resin composition of the present invention is preferably 10 to 100 parts by mass and more preferably 40 to 80 parts by mass with respect to 100 parts by mass of the vinyl chloride resin (Y), from viewpoints of exhibiting excellent compatibility with vinyl chloride resins and obtaining a vinyl chloride resin composition capable of providing a molded article having excellent heat resistance and freeze resistance.

Various additives may be blended with the vinyl chloride resin composition of the present invention within a range not deteriorating the effects of the invention. Examples of the additives include a flame retardant, a stabilizer, a stabilizing aid, a colorant, a processing aid, a filler, an antioxidant (oxidation inhibitor), an ultraviolet absorber, a photostabilizer, a lubricant, an antistatic agent, and a crosslinking aid.

The plasticizer or the additives other than the ester compound (A) or the ester compound (B) may be used alone or in combination of two or more kinds thereof.

Examples of the flame retardant include an inorganic compound such as aluminum hydroxide, antimony trioxide, magnesium hydroxide, or zinc borate; a phosphorus-based compound such as cresyl diphenyl phosphate, tris chloroethyl phosphate, tris chloropropyl phosphate, or tris dichloropropyl phosphate; and a halogen-based compound such as chlorinated paraffin. In the case of blending the vinyl chloride resin composition with the flame retardant, the amount thereof to be blended is normally 0.1 to 20 parts by mass with respect to 100 parts by mass of the vinyl chloride resin (Y).

Examples of the stabilizer include a metal soap compound such as lithium stearate, magnesium stearate, magnesium laurate, calcium ricinoleate, calcium stearate, barium laurate, barium ricinoleate, barium stearate, zinc octoate, zinc laurate, zinc ricinoleate, or zinc stearate; an organotin-based compound such as dimethyltin bis-2-ethylhexyl thioglycolate, dibutyltin maleate, dibutyltin bis butyl maleate, or dibutyltin dilaurate; and an antimony mercaptide compound. In the case of blending the vinyl chloride resin composition with the stabilizer, the amount thereof to be blended is normally 0.1 to 20 parts by mass with respect to 100 parts by mass of the vinyl chloride resin (Y).

Examples of the stabilizing aid include a phosphate-based compound such as triphenyl phosphite, monooctyl diphenyl phosphite, or tridecyl phosphate; a beta-diketone compound such as acetylacetone or benzoylacetone; a polyol compound such as glycerin, sorbitol, pentaerythritol, or polyethylene glycol; a perchlorate compound such as a barium perchlorate salt or a perchloric acid sodium salt; a hydrotalcite compound; and zeolite. In the case of blending the vinyl chloride resin composition with the stabilizing aid, the amount thereof to be blended is normally 0.1 to 20 parts by mass with respect to 100 parts by mass of the vinyl chloride resin (Y).

Examples of the colorant include carbon black, lead sulfide, white carbon, titanium white, lithopone, starch, antimony sulfide, chromium yellow, chromium green, cobalt blue, and molybdenum orange. In the case of blending the vinyl chloride resin composition with the colorant, the amount thereof to be blended is normally 1 part to 100 parts by mass with respect to 100 parts by mass of the vinyl chloride resin (Y).

Examples of the processing aid include a liquid paraffin, a polyethylene wax, stearic acid, stearic acid amide, ethylene bis stearic acid amide, butyl stearate, and calcium stearate. In the case of blending the vinyl chloride resin composition with the processing aid, the amount thereof to be blended is normally 0.1 to 20 parts by mass with respect to 100 parts by mass of the vinyl chloride resin (Y).

Examples of the filler include a metal oxide such as calcium carbonate, silica, alumina, clay, talc, diatomaceous earth, or ferrite; a fiber and powder of glass, carbon, or metal; glass spheres, graphite, aluminum hydroxide, barium sulfate, magnesium oxide, magnesium carbonate, magnesium silicate, and calcium silicate. In the case of blending the vinyl chloride resin composition with the filler, the amount thereof to be blended is normally 1 part to 100 parts by mass with respect to 100 parts by mass of the vinyl chloride resin (Y).

Examples of the antioxidant include a phenolic compound such as 2,6-di-tert-butylphenol, tetrakis[methylene-3-(3,5- tert-butyl-4-hydroxyphenol) propionate] methane, or 2-hydroxy-4-methoxybenzophenone; a sulfur-based compound such as an alkyl disulfide, a thiodipropionate ester, or benzothiazole; a phosphoric acid-based compound such as tris nonylphenyl phosphite, diphenyl isodecyl phosphite, triphenyl phosphite, or tris(2,4-di-tert-butylphenyl) phosphite; and an organic metal-based compound such as zinc dialkyl dithiophosphate or zinc diaryl dithiophosphate. In the case of blending the vinyl chloride resin composition with the antioxidant, the amount thereof to be blended is normally 0.2 to 20 parts by mass with respect to 100 parts by mass of the vinyl chloride resin (Y).

Examples of the ultraviolet absorber include a cyanoacrylate compound, besides a salicylate compound such as phenyl salicylate or p-tert-butylphenyl salicylate; a benzophenone compound such as 2-hydroxy-4-n-octoxybenzophenone or 2-hydroxy-4-n-methoxybenzophenone; and a benzotriazole-based compound such as 5-methyl-1H-benzotriazole or 1-dioctylaminomethylbenzotriazole. In the case of blending the vinyl chloride resin composition with the ultraviolet absorber, the amount thereof to be blended is normally 0.1 to 10 parts by mass with respect to 100 parts by mass of the vinyl chloride resin (Y).

As the photostabilizer, a hindered amine-based photostabilizer may be exemplified. Specific examples thereof include bis(2,2,6,6-tetramethyl-4-piperidyl) sebacate, bis(1,2,2,6,6-pentamethyl-4-piperidyl) sebacate, and methyl 1,2,2,6,6-pentamethyl-4-piperidyl sebacate (mixture), bis(1,2,2,6,6-pentamethyl-4-piperidyl) [[3,5-bis(1,1-dimethylethyl)-4-hydroxyphenyl]methyl]butyl malonate, decanedioic acid bis (2,2,6,6-tetramethyl-1 (octyloxy)-4-piperidyl) ester, a reaction product of 1,1-dimethyl ethyl hydroperoxide and octane, 4-benzoyloxy-2,2,6,6-tetramethylpiperidine, an ester mixture of 2,2,6,6-tetramethyl-4-piperidinol and a higher fatty acid, tetrakis(2,2,6,6-tetramethyl-4-piperidyl)-1,2,3,4-butanete tracarboxylate, tetrakis(1,2,2,6,6-pentamethyl-4-piperidyl)-1,2,3,4-butane tetracarboxylate, a polycondensate of dimethyl succinate and 4-hydroxy-2,2,6,6-tetramethyl-1-piperidineethanol, poly{(6-(1,1,3,3-tetramethylbutyl)amino-1,3,5-triazine-2,4-diyl}{(2,2,6,6-tetramethyl-4-piperidyl)imino} hexamethylene{(2,2,6,6-tetramethyl-4-piperidyl)imino}}, a polycondensate of dibutylamine.1,3,5-triazine.N,N'-bis (2,2,6,6-tetramethyl-4-piperidyl-1,6-hexamethylenediamine and N-(2,2,6,6-tetramethyl-4-piperidyl) butylamine, and N,N',N'',N'''-tetrakis-(4,6-bis-(butyl-(N-methyl-2,2,6,6-tetramethylpiperidin-4-yl) amino)-triazin-2-yl)-4,7-diazadecane-1,10-diamine. In the case of blending the vinyl chloride resin composition with the photostabilizer, the amount thereof to be blended is normally 0.1 to 10 parts by mass with respect to 100 parts by mass of the vinyl chloride resin (Y).

Examples of the lubricant include silicone, liquid paraffin, balafin wax, a fatty acid metal salt such as a metal stearate or a metal laurate salt; fatty acid amides, fatty acid waxes, and higher fatty acid waxes. In the case of blending the vinyl chloride resin composition with the lubricant, the amount thereof to be blended is normally 0.1 to 10 parts by mass with respect to 100 parts by mass of the vinyl chloride resin (Y).

Examples of the antistatic agent include an anionic antistatic agent which is an alkyl sulfonate type, an alkyl ether carboxylic acid type, or a dialkyl sulfosuccinate type; a nonionic antistatic agent such as a polyethylene glycol derivative, a sorbitan derivative, or a diethanolamine derivative; a cationic antistatic agent such as a quaternary ammonium salt which is an alkylamidoamine type or an alkyldimethylbenzyl type, an alkylpyridinium type organic acid salt or hydrochloride; and an amphoteric antistatic agent which is an alkylbetaine type or an alkylimidazoline type. In the case of blending the vinyl chloride resin composition with the antistatic agent, the amount thereof to be blended is normally 0.1 to 10 parts by mass with respect to 100 parts by mass of the vinyl chloride resin (Y).

Examples of the crosslinking aid include polyfunctional monomers such as tetraethylene glycol dimethacrylate, divinylbenzene diallyl phthalate, triallyl isocyanurate, trimethylol propane triallylate, tetramethylol methane tetramethacrylate, and trimethoxy ethoxy vinyl silane, and these are used in a range of 0.5 to 30 parts by mass with respect to 100 parts by mass of the vinyl chloride resin (Y). Specifically, the amount thereof is most effective, in the case where it is 3 to 20 parts by mass.

Regarding the vinyl chloride-based resin composition of the present invention, the plasticizer for a vinyl chloride resin (X) including the ester compound (A1), the vinyl chloride resin (Y), and, if necessary, various additives may be stirred and mixed with each other by a stirrer such as a mortar mixer, HENSCHEL mixer, BUNBURY mixer, or ribbon blender, for example, to obtain mixed powder of the vinyl chloride-based resin composition. In addition, the plasticizer for a vinyl chloride resin (X) including the ester compound (A1), the vinyl chloride resin (Y), and, if necessary, various additives may also be melted and molded by a kneading machine such as a conical twin screw extruder, a parallel twin screw extruder, a single screw extruder, a co-kneader type kneader, or a roll kneader, for example, to obtain a pellet-shaped vinyl chloride-based resin composition. Further, the plasticizer for a vinyl chloride resin (X) including the ester compound (A1), the vinyl chloride resin (Y), specifically, a pellet-shaped vinyl chloride resin, and, if necessary, various additives may also be mixed and kneaded by a kneading machine such as a pony mixer, a butterfly mixer, a planetary mixer, a ribbon blender, a kneader, a dissolver, a biaxial mixer, a high-speed mixer, or a three-roll mill, for example, to obtain a paste-shaped vinyl chloride-based resin composition.

In the case where the blended powder-shaped vinyl chloride resin composition or the pellet-shaped vinyl chloride resin composition is used as the vinyl chloride resin composition of the present invention, a molded article having a desired shape may be obtained by performing melting and molding according to methods well known in the related art, such as vacuum molding, compression molding, extrusion molding, injection molding, calender molding, press molding, blow molding, and powder molding.

Meanwhile, in the case where the paste-shaped vinyl chloride resin composition is used as the vinyl chloride resin composition of the present invention, a molded article having a desired shape may be obtained, by performing molding according to methods well known in the related art, such as spread molding, dipping molding, gravure molding, slush molding, and screen processing.

The shape of the molded body is not particularly limited and examples thereof include a rod shape, a sheet shape, a film shape, a plate shape, a cylindrical shape, a circular shape, and an elliptical shape, or a product having a special shape such as a toy or an ornament, for example, a star shape or a polygonal shape.

The molded body obtained as described above is useful for pipes such as water pipes, joints for pipes, gutters such as rain gutters, automobile materials such as window frame sidings, plates, corrugated plates, car underbody coatings, dashboards, instrument panels, consoles, door sheets, car under carpet, trunk seats, or door trim, various imitation leathers, decoration sheets, agricultural films, films for food packaging, wire coating, various foaming products, hoses, medical tubes, tubes for food, gaskets for refrigerators, packings, wallpaper, flooring materials, boots, curtain, soles, gloves, water stop, toys, panels, blood bags, infusion bags, tarpaulin, mats, impervious sheets, civil engineering sheets, roofing paper, waterproof sheets, insulation sheets, industrial tapes, glass films, and erasers.

The vinyl chloride resin composition of the present invention can be preferably used for preparing wire coating, among the molded bodies. Among the wires obtained by performing the wire coating of the vinyl chloride resin composition of the present invention, a wire harness formed by coating a wire by using the vinyl chloride resin composition of the present invention can be preferably obtained.

In addition, the vinyl chloride resin composition of the present invention can be preferably used for preparing automobile materials as the molded bodies. Among the automobile materials, a dashboard can be preferably obtained by molding the vinyl chloride resin composition of the present invention.

EXAMPLES

Hereinafter, the present invention will be described more specifically with reference to specific examples. In the examples, "parts" and "%" are based on mass, unless otherwise noted. In addition, an acid value, a hydroxyl value, and viscosity were measured in accordance with the following methods.

<Measurement Methods of Acid Value>
The measurement was performed by a method based on JIS K0070-1992.
<Measurement Methods of Hydroxyl Value>
The measurement was performed by a method based on JIS K0070-1992.
<Measurement Methods of Viscosity>
The measurement was performed by a method based on JIS K6901-1986.

Example 1 (Plasticizer for Vinyl Chloride Resin)

296 g (2.0 mol) of phthalic anhydride, 456 g (4.0 mol) of ε-caprolactone, 856 g (4.6 mol) of dodecanol (manufactured by New Japan Chemical Co., Ltd.; CONOL 20P, straight chain percentage: 100 mol %), and 0.438 g of tetraisopropyl titanate as an esterification catalyst were put into a four-neck flask having an inner volume of 2 liters and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted dodecanol was distilled under the reduced pressure at 230° C. to 200° C., and thus, 1,329 g of an ester compound (A2-1) represented by General Formula (2) was obtained. The acid value of the ester compound (A1) was 0.06, the hydroxyl value was 0.06, and the viscosity was 140 mPa·s. According to a GPC chart, 23.9% of the ester compound (A1) in which the total of $a_{21}+a_{22}$ is 1, 19.4% of the ester compound (A1) in which the total of $a_{21}+a_{22}$ is 2, and 13.3% of the ester compound (A1) in which the total of $a_{21}+a_{22}$ is 3, were included. The synthesized ester compound (A2-1) may also be regarded as a plasticizer for a vinyl chloride resin, including the ester compound (A1) [hereinafter, referred to as a "plasticizer for a vinyl chloride resin (1)"].

Example 2 (Same as the Above)

In a reaction vessel, 296 g (2.0 mol) of phthalic anhydride, 456 g (4.0 mol) of ε-caprolactone, 599 g (3.22 mol) of dodecanol (manufactured by New Japan Chemical Co., Ltd.; CONOL 20P, straight chain percentage: 100 mol %), 295 g (1.38 mol) of tetradecanol (manufactured by New Japan Chemical Co., Ltd.; CONOL 1495, straight chain percentage: 100 mol %), and 0.455 g of tetraisopropyl titanate as an esterification catalyst were put into a four-neck flask having an inner volume of 2 liters and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted dodecanol and tetradecanol were distilled under the reduced pressure at 230° C. to 200° C., and thus, 1,365 g of an ester compound (A2-2) represented by General Formula (2) was obtained. The acid value of the ester compound (A2-2) was 0.02, the hydroxyl value was 0.37, and the viscosity was 134 mPa·s. According to a GPC chart, 24.3% of the ester compound (A2-2) in which the total of $a_{21}+a_{22}$ is 1, 15.7% of the ester compound (A2-2) in which the total of $a_{21}+a_{22}$ is 2, and 14.1% of the ester compound (A2-2) in which the total of $a_{21}+a_{22}$ is 3, were included. The synthesized ester compound (A2-2) may also be regarded as a plasticizer for a vinyl chloride resin, including the ester compound (A1) [hereinafter, referred to as a "plasticizer for a vinyl chloride resin (2)"].

Example 3 (Same as the Above)

388 g (2.0 mol) of dimethyl isophthalate, 456 g (4.0 mol) of ε-caprolactone, 856 g (4.6 mol) of dodecanol (manufactured by New Japan Chemical Co., Ltd.; CONOL 20P, straight chain percentage: 100 mol %), and 0.438 g of tetraisopropyl titanate as an esterification catalyst were put into a four-neck flask having an inner volume of 2 liters and being equipped with a thermometer, a stirrer, and a reflux condenser, and gradually heated to 230° C. while stirring under the nitrogen gas stream, the heating was continued at 230° C. until the acid value becomes 2 or lower, generated methanol was continuously removed, and thus, 1,343 g of an ester compound (A2-3) represented by General Formula (2) was obtained. The acid value of the ester compound (A2-3) was 0.04, the hydroxyl value was 0.64, and the viscosity was 175 mPa·s. According to a GPC chart, 10.3% of the ester compound (A2-3) in which the total of $a_{21}+a_{22}$ is 1, 12.1% of the ester compound (A2-3) in which the total of $a_{21}+a_{22}$ is 2, and 20.3% of the ester compound (A2-3) in which the total of $a_{21}+a_{22}$ is 3, were included. The synthesized ester compound (A2-3) may also be regarded as a plasticizer for a vinyl chloride resin, including the ester compound (A1) [hereinafter, referred to as a "plasticizer for a vinyl chloride resin (3)"].

Example 4 (Same as the Above)

388 g (2.0 mol) of dimethyl isophthalate, 456 g (4.0 mol) of ε-caprolactone, 599 g (3.22 mol) of dodecanol (manufactured by New Japan Chemical Co., Ltd.; CONOL 20P, straight chain percentage: 100 mol %), 276 g (1.38 mol) of isotridecanol (manufactured by KH Neochem Co., Ltd.; tridecanol, and 0.444 g of tetraisopropyl titanate as an esterification catalyst were put into a four-neck flask having an inner volume of 2 liters and being equipped with a thermometer, a stirrer, and a reflux condenser, and gradually heated to 230° C. while stirring under the nitrogen gas stream, the heating was continued at 230° C. until the acid value becomes 2 or lower, and generated methanol was continuously removed. After the reaction, the unreacted dodecanol and isotridecanol were distilled under the reduced pressure at 230° C. to 200° C., and thus, 1,330 g of an ester compound (A2-4) represented by General Formula (2) was obtained. The acid value of the ester compound (A2-4) was 0.06, the hydroxyl value was 0.94, and the viscosity was 215 mPa·s. According to a GPC chart, 21.8% of the ester compound (A2-4) in which the total of $a_{21}+a_{22}$ is 1, 20.9% of the ester compound (A2-4) in which the total of $a_{21}+a_{22}$ is 2, and 16.2% of the ester compound (A2-4) in which the total of $a_{21}+a_{22}$ is 3, were included. The synthesized ester compound (A2-4) may also be regarded as a plasticizer for a vinyl chloride resin including the ester compound (A1) [hereinafter, referred to as a "plasticizer for a vinyl chloride resin (4)"].

Example 5 (Same as the Above)

384 g (2.0 mol) of phthalic anhydride, 228 g (2.0 mol) of ε-caprolactone, 580 g (4.46 mol) of n-octanol (straight chain percentage: 100 mol %), 385 g (2.44 mol) of n-decanol (straight chain percentage: 100 mol %), and 0.417 g of tetraisopropyl titanate as an esterification catalyst were put into a four-neck flask having an inner volume of 2 liters and being equipped with a thermometer, a stirrer, and a reflux condenser, and gradually heated to 230° C. while stirring under the nitrogen gas stream, the heating was continued at 230° C. until an acid value becomes 2 or lower, and generated water was continuously removed. After the reaction, the unreacted alcohols were distilled under the reduced pressure at 230° C. to 200° C., and thus, 1,308 g of an ester compound (A3-1) represented by General Formula (3) was obtained. The acid value of the ester compound (A3-1) was 0.08, the hydroxyl value was 0.08, and the viscosity at 25° C. was 150 mPa·s. According to a GPC chart, 36.2% of the ester compound (A3-1) in which the total of $a_{31}+a_{32}+a_{33}$ is 1, 35.8% of the ester compound (A3-1) in which the total of $a_{31}+a_{32}+a_{33}$ is 2, and 14.1% of the ester compound (A3-1) in which the total of $a_{31}+a_{32}+a_{33}$ is 3, were included. The synthesized ester compound (A3-1) may also be regarded as a plasticizer for a vinyl chloride resin, including the ester compound (A1) [hereinafter, referred to as a "plasticizer for a vinyl chloride resin (5)"].

Example 6 (Same as the Above)

159 g (0.83 mol) of phthalic anhydride, 95 g (0.83 mol) of ε-caprolactone, 458 g (2.86 mol) of NEODOL 911 (manufactured by Shell Chemicals Corporation, a mixed alcohol including 18% of nonanol, 42% of decanol, 39% of undecanol, and 1% of octanol, average molecular weight of 160, straight chain percentage: 85%), and 0.187 g of tetraisopropyl titanate as an esterification catalyst were put into a four-neck flask having an inner volume of 1 liter and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted alcohols were distilled under the reduced pressure at 230° C. to 200° C., and thus, 458 g of an ester compound (A3-2) represented by General Formula (3) was obtained. The acid value of the ester compound (A3-2) was 0.18, the hydroxyl value was 0.18, and the viscosity at 25° C. was 177 mPa·s. According to a GPC chart, 35.1% of the ester compound (A3-2) in which the total of $a_{31}+a_{32}+a_{33}$ is 1, 34.2% of the ester compound (A3-2) in which the total of $a_{31}+a_{32}+a_{33}$ is 2, and 13.3% of the ester compound (A3-2) in which the total of $a_{31}+a_{32}+a_{33}$ is 3, were included. The synthesized ester compound (A3-2) may also be regarded as a plasticizer for a vinyl chloride resin including the ester compound (A1) [hereinafter, referred to as a "plasticizer for a vinyl chloride resin (6)"].

Example 7 (Same as the Above)

159 g (0.83 mol) of phthalic anhydride, 95 g of (0.83 mol) of ε-caprolactone, 351 g (2.20 mol) of NEODOL 911, 87 g (0.67 mol) of n-octanol (straight chain percentage: 100 mol %), and 0.182 g of tetraisopropyl titanate as an esterification catalyst were put into a four-neck flask having an inner volume of 1 liter and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted alcohols were distilled under the reduced pressure at 230° C. to 200° C., and thus, 478 g of an ester compound (A3-3) represented by General Formula (3) was obtained. The acid value of the ester compound (A3-3) was 0.15, the hydroxyl value was 0.15, and the viscosity at 25° C. was 174 mPa·s. According to a GPC chart, 36.9% of the ester compound (A3-3) in which the total of $a_{31}+a_{32}+a_{33}$ is 1, 34.8% of the ester compound (A3-3) in which the total of $a_{31}+a_{32}+a_{33}$ is 2, and 14.2% of the ester compound (A3-3) in which the total of $a_{31}+a_{32}+a_{33}$ is 3, were included. The synthesized ester compound (A3-3) may also be regarded as a plasticizer for a vinyl chloride resin including the ester compound (A1) [hereinafter, referred to as a "plasticizer for a vinyl chloride resin (7)"].

Example 8 (Same as the Above)

159 g (0.83 mol) of phthalic anhydride, 95 g (0.83 mol) of ε-caprolactone, 168 g (1.29 mol) of n-octanol (straight chain percentage: 100 mol %), 204 g (1.29 mol) of n-decanol (straight chain percentage: 100 mol %), 53 g (0.29 mol) of n-dodecanol (straight chain percentage: 100 mol %), and 0.180 g of tetraisopropyl titanate as an esterification catalyst were put into a four-neck flask having an inner volume of 1 liter and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted alcohols were distilled under the reduced pressure at 230° C. to 200° C., and thus, 485 g of an ester compound (A3-4) represented by General Formula (3) was obtained. The acid value of the ester compound (A3-4) was 0.15, the hydroxyl value was 0.15, and the viscosity at 25° C. was 160 mPa·s. According to a GPC chart, 34.2% of the ester compound (A3-4) in which the total of $a_{31}+a_{32}+a_{33}$ is 1, 33.8% of the ester compound (A3-4) in which the total of $a_{31}+a_{32}+a_{33}$ is 2, and 13.6% of the ester compound (A3-4) in which the total of $a_{31}+a_{32}+a_{33}$ is 3, were included. The synthesized ester compound (A3-4) may also be regarded as a plasticizer for a vinyl chloride resin including the ester compound (A1) [hereinafter, referred to as a "plasticizer for a vinyl chloride resin (8)"].

Example 9 (Same as the Above)

159 g (0.83 mol) of phthalic anhydride, 95 g (0.83 mol) of ε-caprolactone, 62 g (0.48 mol) of n-octanol (straight chain percentage: 100 mol %), 75 g (0.48 mol) of n-decanol (straight chain percentage: 100 mol %), 137 g (0.95 mol) of isononanol, 178 g (0.95 mol) of n-dodecanol (straight chain percentage: 100 mol %), and 0.185 g of tetraisopropyl titanate as an esterification catalyst were put into a four-neck flask having an inner volume of 1 liter and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted alcohols were distilled under the reduced pressure at 230° C. to 200° C., and thus, 505 g of an ester compound (A3-5) represented by General Formula (3) was obtained. The acid value of the ester compound (A3-5) was 0.18, the hydroxyl value was 0.18, and the viscosity at 25° C. was 180 mPa·s. According to a GPC chart, 35.2% of the ester compound (A3-5) in which the total of $a_{31}+a_{32}+a_{33}$ is 1, 33.8% of the ester compound (A3-5) in which the total of $a_{31}+a_{32}+a_{33}$ is 2, and 16.0% of the ester compound (A3-5) in which the total of $a_{31}+a_{32}+a_{33}$ is 3, were included. The synthesized ester compound (A3-5) may also be regarded as a plasticizer for a vinyl chloride resin including the ester compound (A1) [hereinafter, referred to as a "plasticizer for a vinyl chloride resin (9)"].

Example 10 (Same as the Above)

159 g (0.83 mol) of phthalic anhydride, 95 g (0.83 mol) of ε-caprolactone, 166 g (1.43 mol) of heptanol (straight chain percentage: 880), 266 g (1.43 mol) of n-dodecanol (straight chain percentage: 100 mol %), and 0.180 g of tetraisopropyl titanate as an esterification catalyst were put into a four-neck flask having an inner volume of 1 liter and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted alcohols were distilled under the reduced pressure at 230° C. to 200° C., and thus, 503 g of an ester compound (A3-6) represented by General Formula (3) was obtained. The acid value of the ester compound (A3-6) was 0.18, the hydroxyl value was 0.18, and the viscosity at 25° C. was 167 mPa·s. According to a GPC chart, 34.9% of the ester compound (A3-6) in which the total of $a_{31}+a_{32}+a_{33}$ is 1, 33.5% of the ester compound (A3-6) in which the total of $a_{31}+a_{32}+a_{33}$ is 2, and 15.5% of the ester compound (A3-6) in which the total of $a_{31}+a_{32}+a_{33}$ is 3, were included. The synthesized ester compound (A3-6) may also be regarded as a plasticizer for a vinyl chloride resin including the ester compound (A1) [hereinafter, referred to as a "plasticizer for a vinyl chloride resin (10)"].

Example 11 (Same as the Above)

181 g (0.83 mol) of phthalic anhydride, 95 g (0.83 mol) of ε-caprolactone, 249 g (1.91 mol) of n-octanol (straight chain percentage: 100 mol %), 302 g (1.91 mol) of n-decanol (straight chain percentage: 100 mol %), and 0.180 g of tetraisopropyl titanate as an esterification catalyst were put into a four-neck flask having an inner volume of 1 liter and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted alcohols were distilled under the reduced pressure at 230° C. to 200° C., and thus, 493 g of an ester compound (A4-1) represented by General Formula (4) was obtained. The acid value of the ester compound (A4-1) was 0.15, the hydroxyl value was 0.15, and the viscosity at 25° C. was 328 mPa·s. According to a GPC chart, 33.2% of the ester compound (A4-1) in which the total of $a_{41}+a_{42}+a_{43}+a_{44}$ is 1, 31.4% of the ester compound (A4-1) in which the total of $a_{41}+a_{42}+a_{43}+a_{44}$ is 2, and 14.5% of the ester compound (A4-1) in which the total of $a_{41}+a_{42}+a_{43}+a_{44}$ is 3, were included. The synthesized ester compound (A4-1) may also be regarded to as a plasticizer for a vinyl chloride resin, including the ester compound (A1) [hereinafter, referred to as a "plasticizer for a vinyl chloride resin (11)"].

Comparative Example 1 [Synthesis of Ester Compound (A') for Comparison]

730 g (5.0 mol) of adipic acid, 189 g (1.6 mol) of 1,6-hexanediol, 353 g (3.4 mol) of 2,2-dimethyl-1,3-propanediol, 200 g of (1.75 mol) of ε-caprolactone, 169 g (1.3 mol) of 2-ethylhexanol, and 0.438 g of tetraisopropyl titanate as an esterification catalyst were put into a four-neck flask having an inner volume of 2 liters and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted 1,6-hexanediol, 2,2-dimethyl-1,3-propanediol, and 2-ethylhexanol were distilled under the reduced pressure at 230° C. to 200° C., and thus, 1,358 g of an ester compound (A'1) for comparison was obtained. The acid value of the ester compound (A'1) was 0.1, the hydroxyl value was 9.8, and the viscosity was 6,000 mPa·s. The synthesized ester compound (A'1) for comparison may also be regarded as a plasticizer for a vinyl chloride resin for comparison including the ester compound (A'1) for comparison [hereinafter, referred to as a "plasticizer for a vinyl chloride resin (1') for comparison"].

Comparative Example 2 (Same as the Above)

730 g (5.0 mol) of adipic acid, 283 g (2.4 mol) of 3-methyl-1,5-pentane diol, 250 g (2.4 mol) of 2,2-dimethyl-1,3-propanediol, 171 g (1.5 mol) of ε-caprolactone, 195 g (1.5 mol) of 2-ethylhexanol, and 0.435 g of tetraisopropyl titanate as an esterification catalyst were put into a four-neck flask having an inner volume of 2 liters and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted 3-methyl-1,5-pentane diol, 2,2-dimethyl-1,3-propanediol, and 2-ethylhexanol were distilled under the reduced pressure at 230° C. to 200° C., and thus, 1,430 g of an ester compound (A'2) for comparison was obtained. The acid value of the ester compound (A'2) was 0.1, the hydroxyl value was 10.5, and the viscosity was 3,000 mPa·s. The synthesized ester compound (A'2) for comparison may also be regarded as a plasticizer for a vinyl chloride resin for comparison including the ester compound (A'2) for comparison [hereinafter, referred to as a "plasticizer for a vinyl chloride resin (2') for comparison"].

Comparative Example 3 (Same as the Above)

730 g (5.0 mol) of adipic acid, 126 g (1.4 mol) of 1,4-butanediol, 401 g (3.4 mol) of 3-methyl-1,5-pentane diol, 376 g (1.25 mol) of a hydrogenated castor oil fatty acid, 195 g (1.5 mol) of 2-ethylhexanol, and 0.494 g of tetraisopropyl titanate as an esterification catalyst were put into a four-neck flask having an inner volume of 2 liters and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted 1,4-butanediol, 3-methyl-1,5-pentane diol, and 2-ethylhexanol were distilled under the reduced pressure at 230° C. to 200° C., and thus, 1,532 g of an ester compound (A'3) for comparison was obtained. The acid value of the ester compound (A'3) was 0.1, the hydroxyl value was 11.5, and the viscosity was 3,450 mPa·s. The synthesized ester compound (A'3) for comparison may also be regarded as a plasticizer for a vinyl chloride resin for comparison including the ester compound (A'3) for comparison [hereinafter, referred to as a "plasticizer for a vinyl chloride resin (3') for comparison"].

Comparative Example 4 (Same as the Above)

576 g (3.0 mol) of phthalic anhydride, 1,526 g (9.54 mol) of nonanol (manufactured by Shell Chemicals Corporation; LINEVOL 9, straight chain percentage: 88%), and 0.382 g of tetraisopropyl titanate as an esterification catalyst were put into a four-neck flask having an inner volume of 3 liters and being equipped with a thermometer, a stirrer, and a reflux condenser, and gradually heated to 230° C. while stirring under the nitrogen gas stream, the heating was continued at 230° C. until the acid value becomes 2 or lower, and generated water was continuously removed. After the reaction, the unreacted nonanol was distilled under the reduced pressure at 230° C. to 200° C., the obtained material was neutralized with a 4% sodium hydroxide aqueous solution and filtered, and thus, 1,774 g of an ester compound (A'4) for comparison was obtained. The acid value of the ester compound (A'4) was 0.1, the hydroxyl value was 0.5, and the viscosity was 130 mPa·s. The synthesized ester compound (A'4) for comparison may also be regarded as a plasticizer for a vinyl chloride resin for comparison including the ester compound (A'4) for comparison [hereinafter, referred to as a "plasticizer for a vinyl chloride resin (4') for comparison"].

Example 12 (Vinyl Chloride Resin Composition)

50 parts of the plasticizer for a vinyl chloride resin (1), 100 parts of the vinyl chloride resin [ZEST 1300 manufactured by Shin Dai-Ichi Vinyl Corporation, degree of polymerization of 1,300], and a filler (a calcium/zinc composite stabilizer manufactured by NISSIN TRADING Co., Ltd., product name: GLECK MP-677D) were mixed with each other, and thus, a vinyl chloride resin composition (1) of the present invention was obtained. A molded article was manufactured by using the vinyl chloride resin composition (1), and evaluations of a plasticizing effect of the plasticizer for a vinyl chloride resin (1) with respect to vinyl chloride resins, heat resistance, and freeze resistance were performed. In addition, an evaluation of compatibility between the plasticizer for a vinyl chloride resin (1) and vinyl chloride resins was also performed. Preparing methods and evaluation methods of molded articles used in respective evaluations are shown below. In addition, the evaluation results are shown in Table 1.

Evaluation of Plasticizing Effect of Plasticizer for Vinyl Chloride Resin Including Plasticizer for Vinyl Chloride Resin (1) with Respect to Vinyl Chloride Resins
<Preparing Conditions of Molded Article>

The vinyl chloride resin composition (1) was kneaded with two rolls heated to 170° C., for 10 minutes, the kneaded vinyl chloride resin composition (1) was molded by using a die (die having a thickness of 0.5 mm) by which a molded article having a thickness of 0.5 mm is obtained, and a press machine heated to 170° C., thereby obtaining a sheet having a thickness of 0.5 mm.
<Evaluation Method>

The plasticizing effect was evaluated by measuring a 100% modulus (tensile stress at the time of elongation of 100%) and a tensile elongation percentage in accordance with JIS K6251. Specifically, a tensile test was performed under the following conditions by using the sheet having a thickness of 0.5 mm, thereby measuring the 100% modulus and the tensile elongation percentage. The tensile elongation percentage is a value obtained by subtracting an initial distance between chucks (20 mm) from a distance between chucks at the time when the sheet having a thickness of 0.5 mm was tensile-fractured, dividing the obtained value by the distance between chucks (20 mm), and then expressing the resultant value as a percentage.

Measurement device: "TENSILON Universal Material Testing Instrument" manufactured by A&D Company, Limited Sample shape: Dumbbell-shaped No. 3 Type Distance between chucks: 20 mm Tensile speed: 200 mm/min Measurement atmosphere: temperature of 23° C., humidity of 50%

A low value of the 100% modulus means a high effect of plasticizing vinyl chloride resins. In addition, a high tensile elongation percentage means a high effect of plasticizing vinyl chloride resins.

Evaluation of Heat Resistance of Molded Article of Vinyl Chloride Resin Composition
<Preparing Conditions of Molded Article>

The vinyl chloride resin composition (1) was kneaded with two rolls heated to 170° C., for 10 minutes, the kneaded vinyl chloride resin composition (1) was molded by using a die (die having a thickness of 0.5 mm) by which a molded article having a thickness of 0.5 mm is obtained, and a press machine heated to 170° C., and thus, a sheet having a thickness of 0.5 mm was prepared. A dumbbell-shaped No. 3 type (dumbbell piece) was prepared from the prepared sheet having a thickness of 0.5 mm in accordance with JIS K6251.
<Evaluation Method>

A heat aging test was performed in accordance with JIS K6257. Under the test conditions, 155° C. and 96 hours are set. Mass of the dumbbell piece before and after the heat aging test was measured, and a difference (decreased amount) between the mass before the heat aging test and the mass after the heat aging test was obtained as a percentage on the basis of the mass before the heat aging test. The smaller value indicates that the plasticizer for a vinyl chloride resin (1) is more likely to remain in a molded article even after the heat aging test, and thus, the effect of heat resistance due to the plasticizer (1) for a vinyl chloride resin can be expected.

In addition, a tensile test was performed in accordance with the conditions of JIS K6251 before and after the heat aging test, and elongation percentages of the dumbbell before after the heat aging test were obtained. An elongation percentage (retention of elongation) of the dumbbell piece after the heat aging test was obtained taking the elongation percentage before the heat aging test as a basis (100%). The larger the retention of elongation indicates that the plasticizing effect can be more maintained even after the heat aging test and a vinyl chloride resin composition having excellent heat resistance is provided.

Evaluation of Freeze Resistance of Molded Article of Vinyl Chloride Resin Composition
<Preparing Conditions of Molded Article>

The vinyl chloride resin composition (1) was kneaded with two rolls heated to 170° C., for 10 minutes, the kneaded vinyl chloride resin composition (1) was molded by using a die (die having a thickness of 1.0 mm) by which a molded article having a thickness of 1.0 mm is obtained, and a press machine heated to 170° C., and thus, a sheet having a thickness of 1.0 mm was prepared. A test piece was prepared from the prepared sheet having a thickness of 1.0 mm in accordance with JIS K6745.
<Evaluation Method>

The freeze resistance was evaluated by a Clash-Berg torsion flexibility tester in accordance with JIS K6745. The lower temperature indicates more excellent freeze resistance.

Evaluation of Compatibility
<Preparing Conditions of Molded Article>

The vinyl chloride resin composition (1) was kneaded with two rolls heated to 170° C., for 10 minutes, the kneaded vinyl chloride resin composition (1) was molded by using a die (die having a thickness of 1.0 mm) by which a molded article having a thickness of 1.0 mm is obtained, and a press machine heated to 170° C., and thus, a sheet having a thickness of 1.0 mm was prepared. Two sheets having a thickness of 1.0 mm which was cut out from the sheet to have a size of 5 cm×5 cm were prepared.
<Evaluation Methods>

Two sheets were overlapped on each other and left under the conditions of 70° C. and a relative humidity of 95% for 7 days. After that, the states of the front surfaces of the sheets and the surfaces of the sheets overlapped on each other were evaluated based on the following evaluation criteria.

A: When the front surfaces of the sheets and the surfaces of the sheets overlapped on each other were visually observed, powder-shaped or viscous foreign materials (bleeding) cannot be confirmed and, even in the case where the front surfaces of the sheets and the surfaces of the sheets overlapped on each other were touched by fingers, the bleeding cannot be confirmed.

B: When the front surfaces of the sheets and the surfaces of the sheets overlapped on each other were visually observed, the bleeding can be confirmed, or when the front surfaces of the sheets and the surfaces of the sheets overlapped on each other were touched by fingers, the bleeding can be confirmed.

Example 13 (Same as the Above)

A vinyl chloride resin composition (2) was obtained in the same manner as in Example 12, except that 50 parts of the plasticizer for a vinyl chloride resin (2) was used, instead of using 50 parts of the plasticizer for a vinyl chloride resin (1). The same evaluations as those in Example 12 are performed and the results are shown in Table 1.

Example 14 (Same as the Above)

A vinyl chloride resin composition (3) was obtained in the same manner as in Example 12, except that 50 parts of the plasticizer for a vinyl chloride resin (3) was used, instead of using 50 parts of the plasticizer for a vinyl chloride resin (1). The same evaluations as those in Example 12 are performed and the results are shown in Table 1.

Example 15 (Same as the Above)

A vinyl chloride resin composition (4) was obtained in the same manner as in Example 12, except that 50 parts of the plasticizer for a vinyl chloride resin (4) was used, instead of using 50 parts of the plasticizer for a vinyl chloride resin (1). The same evaluations as those in Example 12 are performed and the results are shown in Table 1.

Example 16 (Same as the Above)

A vinyl chloride resin composition (5) was obtained in the same manner as in Example 12, except that 50 parts of the plasticizer for a vinyl chloride resin (5) was used, instead of using 50 parts of the plasticizer for a vinyl chloride resin (1). The same evaluations as those in Example 12 are performed and the results are shown in Table 2.

Evaluation Method of Oil Resistance
<Test Piece>

The dumbbell-shaped No. 3 type (dumbbell piece) disclosed in the section of "Evaluation of Heat Resistance of Molded Article of Vinyl Chloride Resin Composition" was used.
<Evaluation Method>

An oil resistance test was performed in accordance with JIS K6258. Under the test conditions, 100° C. and 72 hours are set. A solution for the test is JIS No. 2 insulation oil (product name: Transformer Oil G manufactured by Idemitsu Kosan Co., Ltd.). The mass of the dumbbell piece before and after the oil resistance test was measured, and a difference (decreased amount) between the mass before the oil resistance test and the mass after the oil resistance was obtained as a percentage on a basis of the mass before the oil resistance test. The smaller value indicates that the plasticizer for a vinyl chloride resin (5) is more likely to remain in a molded article even after the oil resistance test, and thus, the effect of oil resistance due to the plasticizer (5) for a vinyl chloride resin can be expected.

Example 17 (Same as the Above)

A vinyl chloride resin composition (6) was obtained in the same manner as in Example 12, except that 50 parts of the plasticizer for a vinyl chloride resin (6) was used, instead of using 50 parts of the plasticizer for a vinyl chloride resin (1). The same evaluations as those in Example 16 are performed and the results are shown in Table 2.

Example 18 (Same as the Above)

A vinyl chloride resin composition (7) was obtained in the same manner as in Example 12, except that 50 parts of the plasticizer for a vinyl chloride resin (7) was used, instead of using 50 parts of the plasticizer for a vinyl chloride resin (1).

The same evaluations as those in Example 16 are performed and the results are shown in Table 2.

Example 19 (Same as the Above)

A vinyl chloride resin composition (8) was obtained in the same manner as in Example 12, except that 50 parts of the plasticizer for a vinyl chloride resin (8) was used, instead of using 50 parts of the plasticizer for a vinyl chloride resin (1). The same evaluations as those in Example 16 are performed and the results are shown in Table 2.

Example 20 (Same as the Above)

A vinyl chloride resin composition (9) was obtained in the same manner as in Example 12, except that 50 parts of the plasticizer for a vinyl chloride resin (9) was used, instead of using 50 parts of the plasticizer for a vinyl chloride resin (1). The same evaluations as those in Example 16 are performed and the results are shown in Table 2.

Example 21 (Same as the Above)

A vinyl chloride resin composition (10) was obtained in the same manner as in Example 12, except that 50 parts of the plasticizer for a vinyl chloride resin (10) was used, instead of using 50 parts of the plasticizer for a vinyl chloride resin (1). The same evaluations as those in Example 16 are performed and the results are shown in Table 2.

Example 22 (Same as the Above)

A vinyl chloride resin composition (11) was obtained in the same manner as in Example 12, except that 50 parts of the plasticizer for a vinyl chloride resin (11) was used, instead of using 50 parts of the plasticizer for a vinyl chloride resin (1). The same evaluations as those in Example 16 are performed and the results are shown in Table 2.

Example 23 (Same as the Above)

A vinyl chloride resin composition (12) was obtained in the same manner as in Example 12, except that 40 parts of the plasticizer for a vinyl chloride resin (1) and 10 parts of tri-2-ethylhexyl trimellitate were used. The same evaluations as those in Example 12 are performed, and a degree of difficulty of transfer (non-transfer properties) of a plasticizer for a vinyl chloride resin (12) to an ABS resin, in the case where a molded article obtained by using the plasticizer for a vinyl chloride resin (12) and the ABS resin was brought into contact with each other, was evaluated in accordance with the following method. The evaluation results are shown in Table 3.
<Preparing Conditions of Molded Article>
A sheet having a thickness of 1.0 mm was prepared in accordance with the section "<Preparing Conditions of Molded Article>" of the section "Evaluation of Compatibility", and two sheets having a thickness of 1.0 mm which was cut out from the sheet to have a rectangular shape of 0.6 cm×3.8 cm were prepared.
The sheet was sandwiched between two flat plates formed of the ABS resin (manufactured by Asahi Kasei Corporation, product name: STYLAC Grade 121), and left at 70° C., under load conditions of 0.22 kg/cm² for 72 hours. After being left, the surface of the flat plate of the ABS resins was visually observed, and evaluation was performed based on the following evaluation criteria.

A: Even in the case where the surface of the flat plate is irradiated with light and visually observed, rectangular traces (transfer traces) cannot be observed, or, although transfer traces can be confirmed, the traces can be removed by wiping the surface by gauze impregnated with ethanol.
B: When the surface of the flat plate was wiped by gauze impregnated with ethanol and then observed carefully while emitting light, slight transfer races can be confirmed.
C: When the surface of the flat plate was wiped by gauze impregnated with ethanol and then observed, clear transfer races can be confirmed.

Example 24 (Same as the Above)

A vinyl chloride resin composition (13) was obtained in the same manner as in Example 12, except that 40 parts of the plasticizer for a vinyl chloride resin (1) and 10 parts of tetra-2-ethylhexyl pyromellitate were used. The same evaluations as those in Example 23 are performed and the results are shown in Table 3.

Comparative Example 5 (Vinyl Chloride Resin Composition for Comparison)

A vinyl chloride resin composition (1') was obtained in the same manner as in Example 12, except that 50 parts of the ester compound (A'1) for comparison was used, instead of using 50 parts of the ester compound (A1). The same evaluations as those in Example 12 are performed and the results are shown in Table 4.

Comparative Example 6 (Same as the Above)

A vinyl chloride resin composition (2') was obtained in the same manner as in Example 12, except that 50 parts of the ester compound (A'2) for comparison was used, instead of using 50 parts of the ester compound (A1). The same evaluations as those in Example 12 are performed and the results are shown in Table 4.

Comparative Example 7 (Same as the Above)

A vinyl chloride resin composition (3') was obtained in the same manner as in Example 12, except that 50 parts of the ester compound (A'3) for comparison was used, instead of using 50 parts of the ester compound (A1). The same evaluations as those in Example 12 are performed and the results are shown in Table 4.

Comparative Example 8 (Same as the Above)

A vinyl chloride resin composition (4') was obtained in the same manner as in Example 12, except that 50 parts of the ester compound (A'4) for comparison was used, instead of using 50 parts of the ester compound (A1). The same evaluations as those in Example 12 are performed and the results are shown in Table 4.

Comparative Example 9 (Same as the Above)

A vinyl chloride resin composition (5') was obtained in the same manner as in Example 12, except that 50 parts of tri-2-ethylhexyl trimellitate (acid value of 0.1, hydroxyl value of 0.6, and viscosity 210 mPa·s) was used, instead of using 50 parts of the ester compound (A1). The same evaluations as those in Example 12 are performed and the results are shown in Table 4.

Comparative Example 10 (Same as the Above)

A vinyl chloride resin composition (6') was obtained in the same manner as in Example 12, except that 50 parts of trinormal octyl trimellitate (acid value of 0.1, hydroxyl value of 0.1, and viscosity 90 mPa·s) was used, instead of using 50 parts of the ester compound (A1). The same evaluations as those in Example 12 are performed and the results are shown in Table 4.

TABLE 1

| | Example | | | |
|---|---|---|---|---|
| Evaluation item | 12 | 13 | 14 | 15 |
| Plasticizing effect [100% modulus (MPa)] | 13.1 | 13.5 | 13.6 | 13.8 |
| Plasticizing effect [elongation percentage (%)] | 292 | 284 | 298 | 294 |
| Heat resistance [heat aging decreased amount (%)] | 4.3 | 3.7 | 3.1 | 3.3 |
| Heat resistance [retention of elongation (%)] | 82 | 77 | 84 | 80 |
| C/B low temperature softening temperature (° C.) | −27 | −28 | −29 | −27 |
| Compatibility (presence or absence of bleeding) | A | A | A | A |

TABLE 2

| | Example | | | | | | |
|---|---|---|---|---|---|---|---|
| Evaluation item | 16 | 17 | 18 | 19 | 20 | 21 | 22 |
| Plasticizing effect [100% modulus (MPa)] | 14.1 | 14.8 | 14.5 | 14.5 | 14.7 | 14.4 | 15.2 |
| Plasticizing effect [elongation percentage (%)] | 332 | 296 | 300 | 306 | 286 | 280 | 310 |
| Heat resistance [heat aging decreased amount (%)] | 2 | 1.8 | 1.6 | 1.7 | 1.7 | 1.9 | 1.1 |
| Heat resistance [retention of elongation (%)] | 91 | 88 | 92 | 93 | 92 | 97 | 92 |
| C/B low temperature softening temperature (° C.) | −24 | −26 | −26 | −27 | −26 | −26 | −22 |
| Compatibility (presence or absence of bleeding) | A | A | A | A | A | A | A |
| Oil resistance [decreased amount (%)] | 9.0 | 6.9 | 7.2 | 8.3 | 6.9 | 7.5 | 2.0 |

TABLE 3

| | Example | |
|---|---|---|
| Evaluation item | 23 | 24 |
| Plasticizing effect [100% modulus (MPa)] | 14.2 | 13.9 |
| Plasticizing effect [elongation percentage (%)] | 320 | 308 |
| Heat resistance [heat aging decreased amount (%)] | 4.7 | 3.1 |
| Heat resistance [retention of elongation (%)] | 78 | 85 |
| C/B low temperature softening temperature (° C.) | −27 | −26 |
| Compatibility (presence or absence of bleeding) | A | A |
| Non-transfer properties | A | B |

TABLE 4

| Evaluation item | Comparative Example 5 | Comparative Example 6 | Comparative Example 7 | Comparative Example 8 | Comparative Example 9 | Comparative Example 10 |
|---|---|---|---|---|---|---|
| Plasticizing effect [100% modulus (MPa)] | 14.2 | 14.2 | 14.3 | 14.3 | 14.8 | 13.7 |
| Plasticizing effect [elongation percentage (%)] | 260 | 270 | 270 | 329 | 300 | 311 |
| Heat resistance [heat aging decreased amount (%)] | 1.7 | 2.2 | 2.1 | 2.7 | 10.1 | 3.5 |
| Heat resistance [retention of elongation (%)] | 98 | 96 | 97 | 92 | 45 | 94 |
| C/B low temperature softening temperature (° C.) | −10 | −11 | −12 | −28 | −17 | −27 |
| Compatibility (presence or absence of bleeding) | A | A | A | B | A | A |

The invention claimed is:

1. A vinyl chloride resin composition comprising a plasticizer for a vinyl chloride resin and a vinyl chloride resin wherein the plasticizer for a vinyl chloride resin comprising:
   an ester compound (A1) represented by General Formula (1):

[Chem. 1]

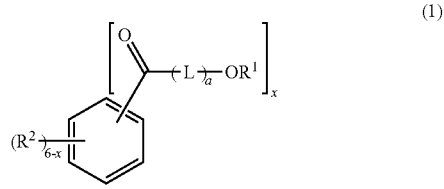

(1)

wherein x is an integer of 2 to 4, plural L's may be the same or different, plural $R^1$'s may be the same or different, plural $R^2$'s may be the same or different, L's each represent an aliphatic oxycarboxylic acid residue having 3 to 18 carbon atoms or a cyclic ester residue having 3 to 18 carbon atoms, $R^1$'s each represent an alkyl group having 6 to 18 carbon atoms, $R^2$'s each represent a hydrogen atom or an alkyl group having 1 to 6 carbon atoms, and plural a's each represents a repeating number of L, provided that the total of the plural a's is from 1 to 10, and
wherein the ester compound (A1) is produced by a reaction between benzenecarboxylic acid, which is one or more compounds selected from the group consisting of phthalic acid, isophthalic acid, terephthalic acid, trivalent benzenecarboxylic acid, tetravalent benzenecarboxylic acid, alkyl esters thereof, and phthalic acid anhydride; a cyclic ester selected from the group consisting of ε-caprolactone, methyl-ε-caprolactone, and dimethyl-ε-caprolactone; and a saturated aliphatic monoalcohol selected from the group consisting of dodecanol, tridecanol, tetradecanol, isotridecanol, pentadecanol, and hexadecanol, or a mixture of saturated aliphatic monoalcohols consisting of monoalcohols having alkyl group with 6 to 18 carbon atoms and the saturated aliphatic monoalcohol selected from the group consisting of dodecanol, tridecanol, tetradecanol, isotridecanol, pentadecanol, and hexadecanol, wherein the saturated aliphatic monoalcohol or the mixture of saturated aliphatic monoalcohols having a straight chain percentage of 85 mol % or more, and wherein the content of the plasticizer for a vinyl chloride resin is from 10 to 100 parts by mass with respect to 100 parts by mass of the vinyl chloride resin.

2. The vinyl chloride resin composition according to claim 1, wherein the ester compound (A1) is an ester compound represented by General Formula (2-1), General Formula (2-2), or General Formula (2-3):

[Chem. 2]

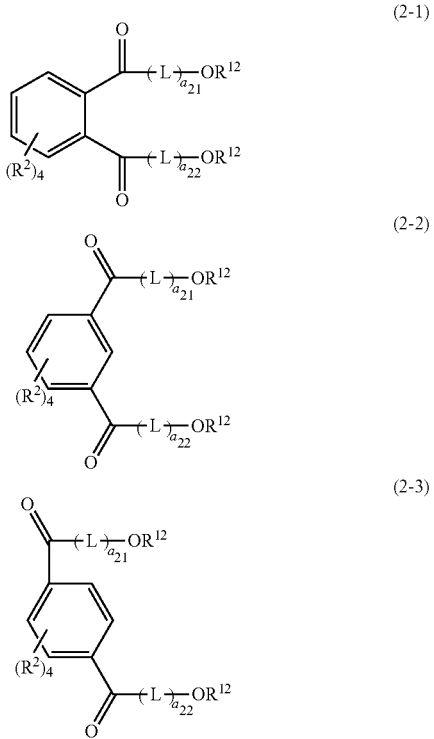

wherein L and $R^2$ are the same as defined above and $R^{12}$'s each are an alkyl group having 6 to 18 carbon atoms; and plural $a_{21}$ and plural $a_{22}$'s each represents a repeating number of L.

3. The vinyl chloride resin composition according to claim 2, wherein the ester compound (A1) is an ester compound represented by General Formula (2-1), General Formula (2-2), or General Formula (2-3), and the ester compound represented by General Formula (2-1), General Formula (2-2), or General Formula (2-3) is a mixture of compounds being different in the total of $a_{21}$ and $a_{22}$, and the mixture includes an ester compound with the total of $a_{21}$ and $a_{22}$ being 2 or 3 in an amount of 10% to 100% as a percentage of a peak area with respect to each molecular weight obtained by gel permeation chromatography (GPC) measurement.

4. The vinyl chloride resin composition according to claim 1, wherein X in General Formula (1) is 3.

5. The vinyl chloride resin composition according to claim 4, wherein the ester compound (A1) is an ester compound represented by General Formula (3-1):

[Chem. 3]

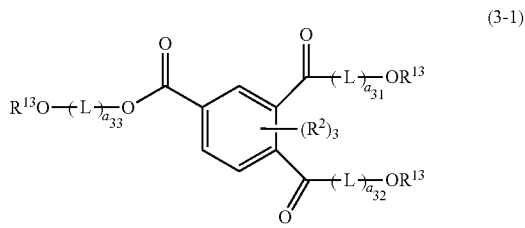

wherein L and $R^2$ are the same as defined above, the total of $a_{31}$, $a_{32}$, and $a_{33}$ is from 1 to 10, and $R^{13}$'s each are an alkyl group having 6 to 18 carbon atoms.

6. The vinyl chloride resin composition according to claim 5, wherein the ester compound (A1) is an ester compound represented by General Formula (3-1), the ester compound is a mixture of compounds different in the total of $a_{31}$, $a_{32}$, and $a_{33}$, and the mixture includes an ester compound with the total of $a_{31}$, $a_{32}$, and $a_{33}$ being 1 or 2 in an amount of 10% to 100% as a percentage of a peak area with respect to each molecular weight obtained by a gel permeation chromatography (GPC) measurement.

7. The vinyl chloride resin composition according to claim 1, wherein the plasticizer for a vinyl chloride resin further comprising:

an ester compound (B) of an aromatic carboxylic acid and a saturated aliphatic monoalcohol having 4 to 12 carbon atoms.

8. The vinyl chloride resin composition according to claim 7, wherein the ester compound (B) is an ester compound of trimellitic acid and 2-ethylhexanol.

9. The vinyl chloride resin composition according to claim 7, wherein the ester compound (B) is an ester compound of pyromellitic acid and 2-ethylhexanol.

10. The vinyl chloride resin composition according to claim 7, wherein the content of the ester compound (B) is from 10 to 300 parts by mass with respect to 100 parts by mass of the ester compound (A1).

11. A wire harness which is formed by coating a wire with the vinyl chloride resin composition according to claim 1.

12. A dashboard which is formed by molding the vinyl chloride resin composition according to claim 1.

13. The vinyl chloride resin composition according to claim 1, wherein the amount of the cyclic ester in producing the ester compound (A1) is 0.1 mol to 1 mol with respect to 1 mol of the carboxyl group in the benzenecarboxylic acid.

14. The vinyl chloride resin composition according to claim 1, wherein the vinyl chloride resin composition has a low temperature softening temperature of −24° C. to −29° C.

* * * * *